United States Patent
Sandler et al.

(10) Patent No.: US 9,795,660 B2
(45) Date of Patent: Oct. 24, 2017

(54) ID-PROTEIN TARGETED TUMOR CELL VACCINE

(71) Applicant: Children's National Medical Center, Washington, DC (US)

(72) Inventors: Anthony Sandler, Bethesda, MD (US); Lina Chakrabarti, Silver Spring, MD (US)

(73) Assignee: Children's National Medical Center, Washington, DC (US)

( * ) Notice: Subject to any disclaimer, the term of this patent is extended or adjusted under 35 U.S.C. 154(b) by 0 days.

(21) Appl. No.: 14/981,114

(22) Filed: Dec. 28, 2015

(65) Prior Publication Data

US 2016/0310582 A1    Oct. 27, 2016

Related U.S. Application Data

(60) Provisional application No. 62/096,792, filed on Dec. 24, 2014, provisional application No. 62/096,788, filed on Dec. 24, 2014.

(51) Int. Cl.
| | | |
|---|---|---|
| A61K 39/00 | (2006.01) |
| A61K 39/395 | (2006.01) |
| C12N 5/09 | (2010.01) |
| C07K 14/47 | (2006.01) |

(52) U.S. Cl.
CPC ...... *A61K 39/0011* (2013.01); *C07K 14/4702* (2013.01); *C12N 5/0693* (2013.01); *A61K 39/3955* (2013.01); *A61K 2039/505* (2013.01); *A61K 2039/5152* (2013.01); *C12N 2501/60* (2013.01); *C12N 2510/00* (2013.01)

(58) Field of Classification Search
None
See application file for complete search history.

(56) References Cited

U.S. PATENT DOCUMENTS

| 6,852,318 B1* | 2/2005 | Varner | A61K 38/08 |
| | | | 424/130.1 |
| 2004/0197328 A1* | 10/2004 | Young | A61K 47/48569 |
| | | | 424/141.1 |
| 2007/0020646 A1* | 1/2007 | Hoon | C12Q 1/6886 |
| | | | 435/6.11 |

OTHER PUBLICATIONS

Wang et al. (J. Immunol. 1998 161: 5516-5524).*
Guéry et al. (J. Immunol. 1995 154:536-544).*
de Jong et al (Immunology, 2006, 119:499-506).*
Gura (Science, 1997, 278:1041-1042).*
Kaiser (Science, 2006, 313: 1370).*
Gerdes et al. (Front. Oncol. Dec. 18, 2014 doi: 10.3389/fonc.2014.00366, pp. 1-12).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Dillman (Annals of Internal Medicine, 1989 111:592-603).*

* cited by examiner

*Primary Examiner* — Peter J Reddig
(74) *Attorney, Agent, or Firm* — Oblon, McClelland, Maier & Neustadt, L.L.P.

(57) ABSTRACT

ID Protein targeted cancer immunotherapy. The invention provides a cell-based attenuated live tumor cell vaccine that safely produces broad cellular tumor-specific immunity, protects against tumor formation in prophylactic tumor models, and in combination with the clinically relevant immune modulator s such as antibodies to CTLA-4 or antibodies to PD-L1 can destroy established tumors in mammals.

7 Claims, 20 Drawing Sheets
(15 of 20 Drawing Sheet(s) Filed in Color)

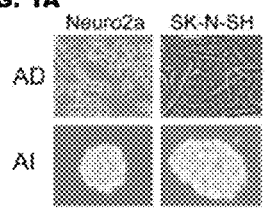
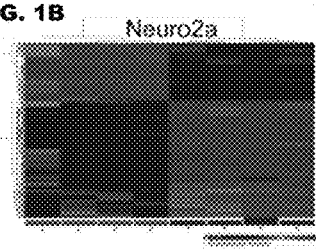
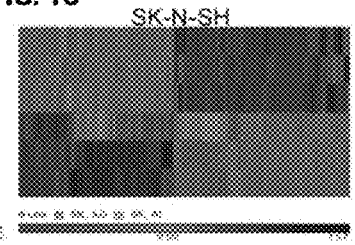
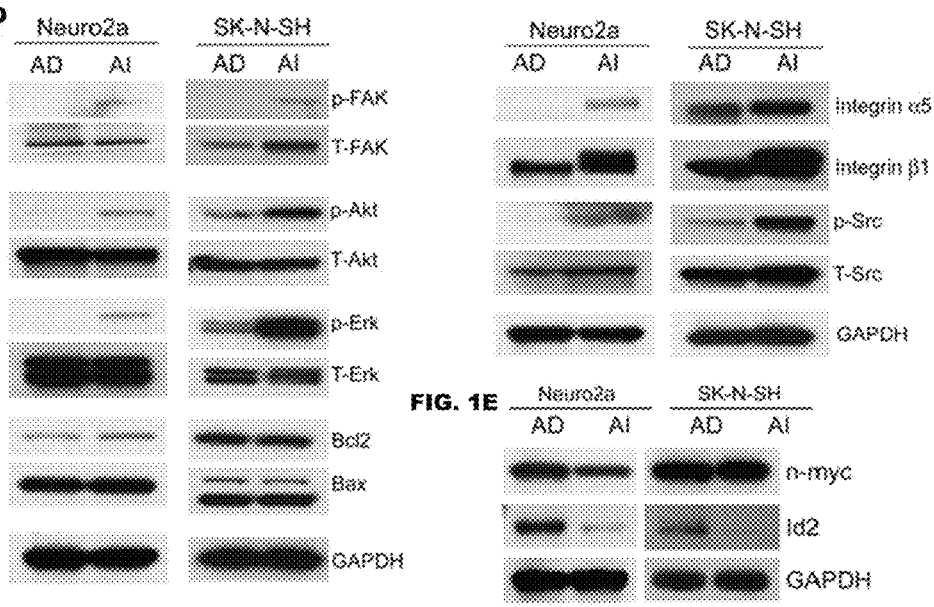

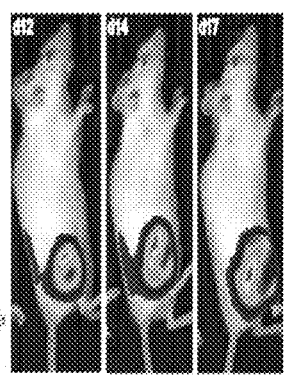
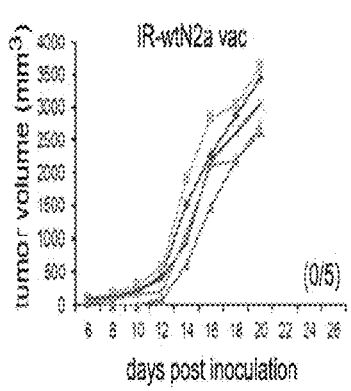
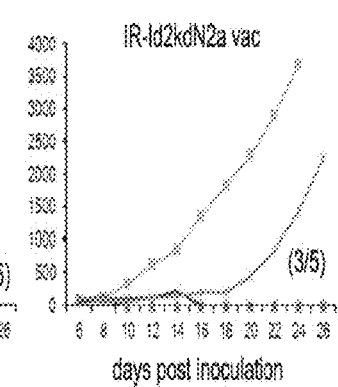
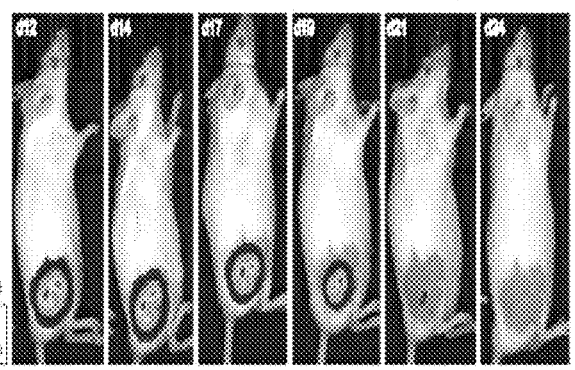
FIG. 9A
FIG. 9C
FIG. 9D
FIG. 9B

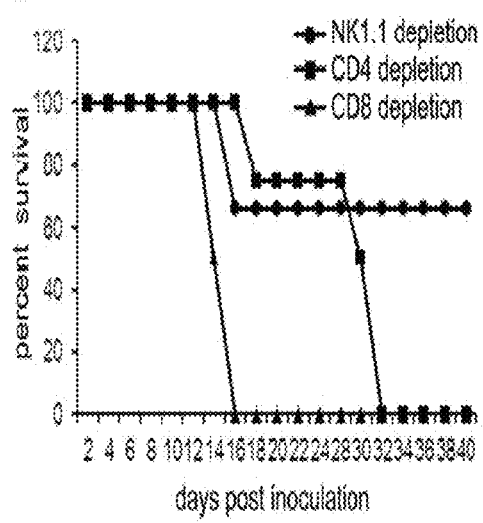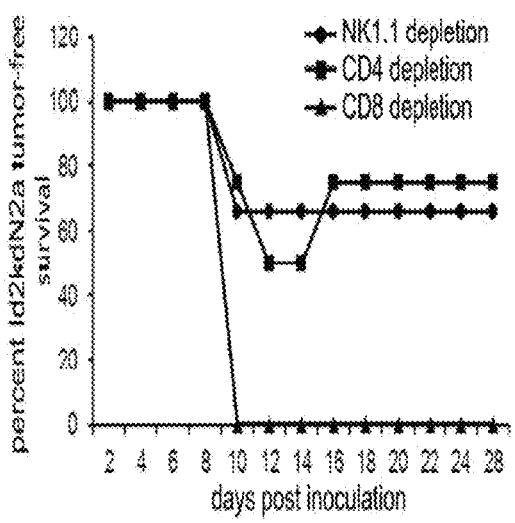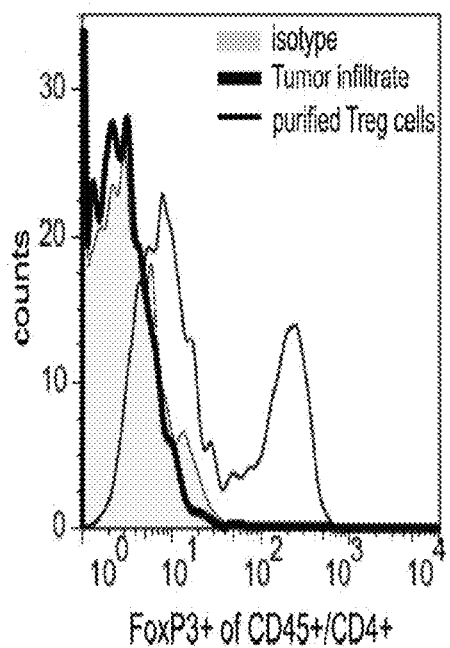

FIG. 13A
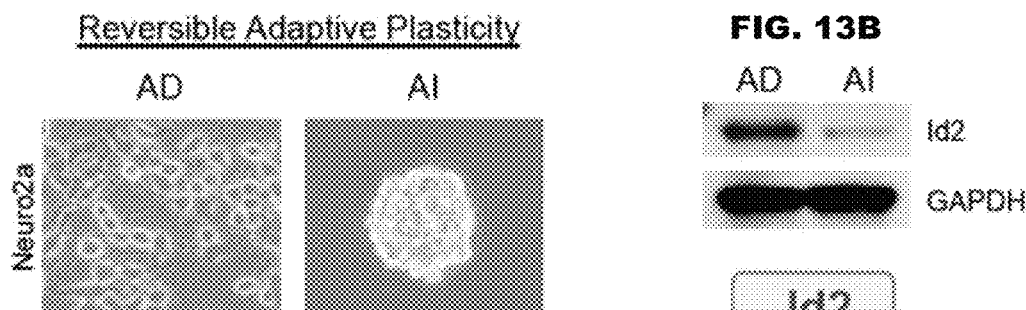
FIG. 13B
FIG. 13C
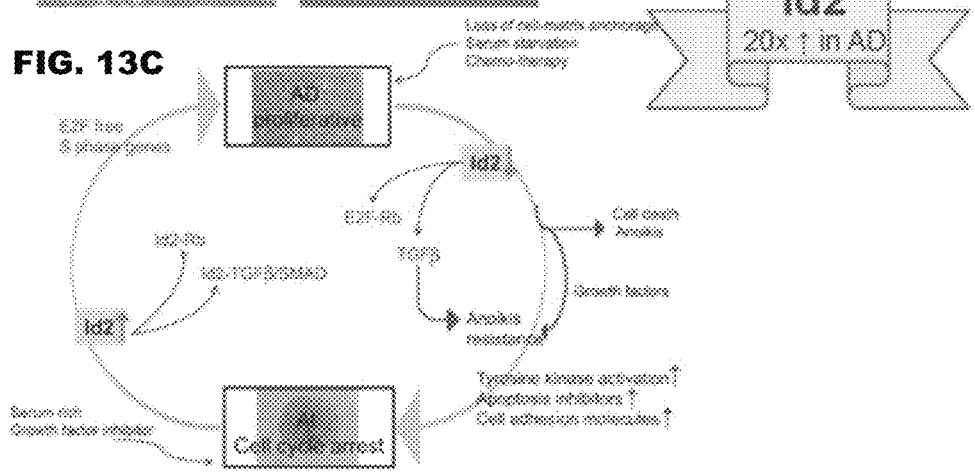
FIG. 13D
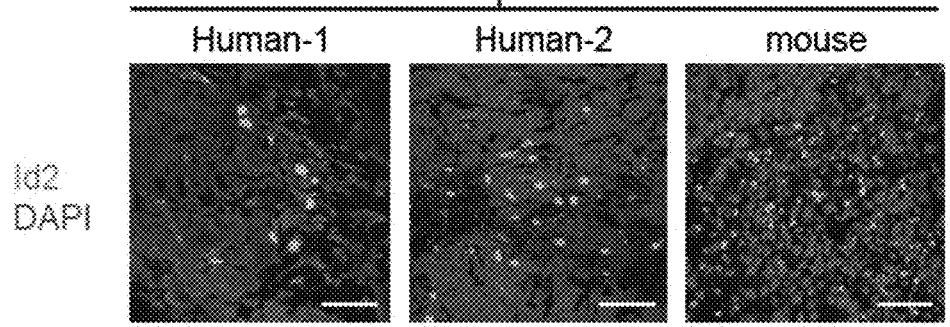

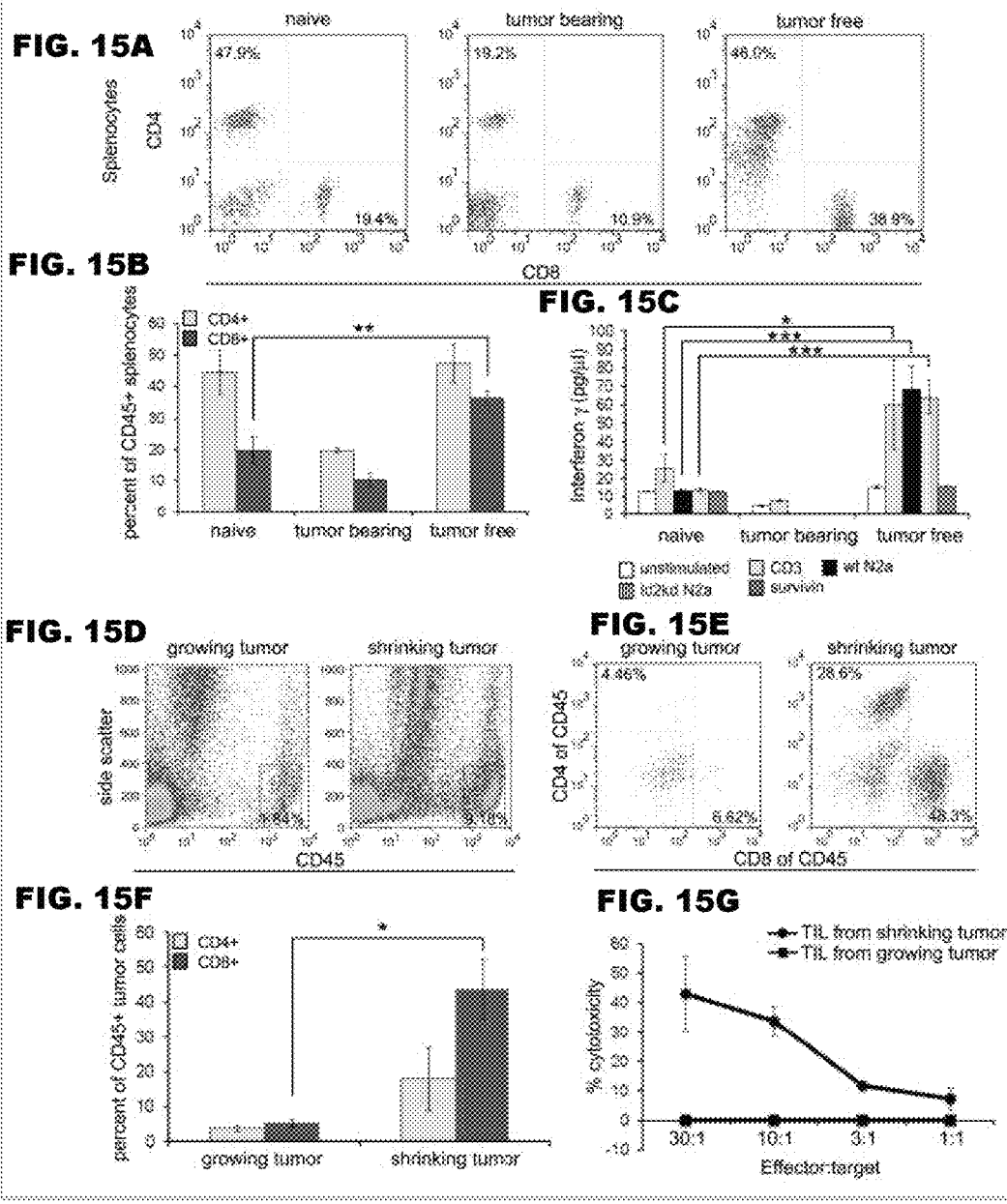

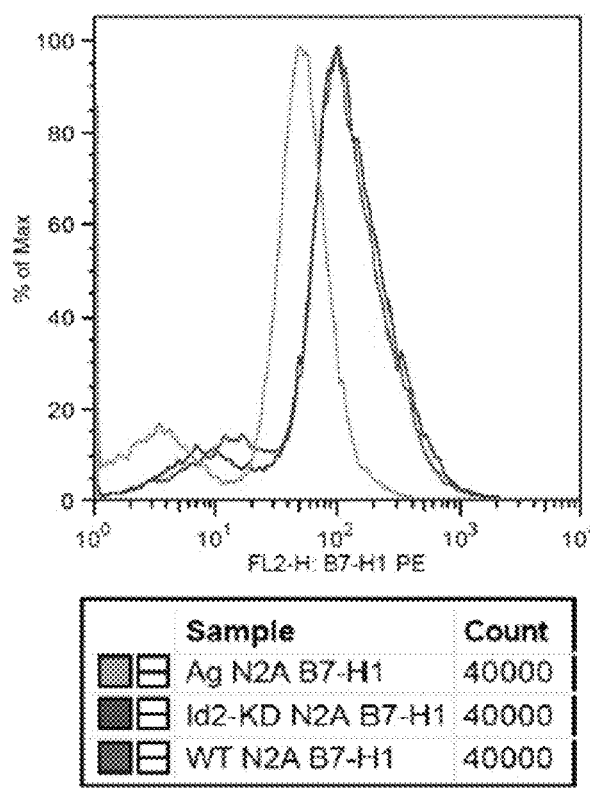
FIG. 16A Gene array: PD-L1 expression
N2a 3.7 fold > AgN2a

ID-PROTEIN TARGETED TUMOR CELL VACCINE

CROSS-REFERENCE TO RELATED APPLICATIONS

This application claims priority to U.S. Provisional Application No. 62/096,788, filed Dec. 24, 2014 and to U.S. Provisional Application No. 62/096,792, filed Dec. 24, 2014. Both of these priority documents are incorporated by reference in their entireties.

REFERENCE TO SEQUENCE LISTING

In accordance with MPEP 502.05(L), the present specification makes reference to a Sequence Listing (submitted electronically as a .txt file named "13861393_1.txt" on Dec. 28, 2015. The .txt file was generated on Feb. 24, 2015 and is 39.9 kb in size. The entire contents of the Sequence Listing are herein incorporated by reference.

BACKGROUND OF THE INVENTION

Field of the Invention

Cancer immunotherapy based on knocking out or attenuating inhibitor of differentiation proteins (ID proteins) to increase the immunogenicity of tumor, neoplastic or cancer cells.

Related Art

Cancer is the leading cause of death in developed countries and the second leading cause of death in developing countries. While localized tumors are often responsive to therapy, patients with unfavorable tumors and high-risk neoplastic diseases, including inoperative tumors, malignant tumors, metastatic tumors, massive tumors, and other tumors resistant to conventional treatment, have dismal survival rates despite multi-modal therapies. Immunotherapy is an attractive alternative therapeutic option as it potentially offers a more specific treatment than conventional therapies. However, to date, immunotherapies in the form of cancer vaccines have held promise but offered little success.

Id proteins, such as Id2, have been previously associated with apoptosis and cancer. Cao, et al., Oncogene: 28(8): 1089-98 (2009) indicated that TGF-beta repression of Id2 induced apoptosis in gut epithelial cells. Zhang, et al. Tumori 100(3): 352-7 (2014) reported that upregulation of Id2 antagonized arsenic trioxide-induced antitumor effects in cancer cells. Zhao, et al., Tumour Biol. 36(6): 4189-96 (2015) reported that silencing Id2 promoted apoptosis of glioblastoma cells, which was attributed to effects that Id2 has on tumor cell chemosensitivity. However, prior studies did not report the effects of knocking out or attenuating Id protein expression on the recognition of tumor cells by the immune system.

BRIEF SUMMARY OF THE INVENTION

The inventors have found that modifying tumor or cancer cells by attenuating or knock-out Id protein expression renders the modified cells more immunogenic and capable of inducing immune responses that render unmodified tumor cells subject to recognition, attack and destruction by the immune system. Immune responses engendered by immunization of a subject with the modified tumor and cancer cells according to the invention may be further enhanced by checkpoint modulation, such as by blocking CTLA-4 during T-cell priming and by blocking PD-L1 present on tumor or cancer cells during effector phase.

The invention provides a cell-based tumor cell vaccine that safely produces broad tumor-specific immunity, protects against tumor formation in prophylactic tumor models, and in combination with the clinically relevant immune modulator such as antibodies to CTLA-4 or antibodies to PD-L1, can destroy established tumors in mammals. Nonlimiting aspects of this technology include the following.

A modified tumor, neoplastic, or cancer cell that expresses less Id protein than an unmodified cell or a modified cell in which the activity of an Id protein has been eliminated or attenuated compared to an otherwise unmodified tumor, neoplastic, or cancer cell. Modified cells may be incorporated into immunogenic compositions suitable for administration to a subject having cancer. Such modified cells may also be incorporated into compositions suitable for priming and inducing cellular immune responses ex vivo or in vitro to tumor, neoplastic, or cancer antigens, cells, or tissues. An immunogenic composition may further comprise immunomodulators, such as antibodies that bind to CTLA-4 and/or PD-L1 (see FIG. 18), to the natural ligands of CTLA-4 or PD-L1, or to other checkpoint determinants. Other examples of immunomodulators include antibodies or other antagonists that block the interaction of CTLA-4 or PD-L1 with their respective ligands, such as B7 or PD-1. The inventors have found that immunogenic compositions containing the cells modified to eliminate or attenuate expression or functional activity of Id proteins can successfully be used as cancer prevention vaccine, a cancer treatment vaccine, or a biological therapy for cancer.

Unmodified cells used to produce the modified cells, immunogenic composition, and anti-tumor vaccines according to the invention are preferably cancer, neoplastic, or tumor cells. However, an unmodified cell may also be a normal cell that carries or has been engineered to express a tumor-specific or tumor-associated antigen. Preferably, the cell to be modified is an autologous cell to avoid the risk of inducing autoimmune responses. However, allogeneic or xenogeneic cells may also be modified.

In some cases, the modified cell will be produced from an unmodified cancer, neoplastic or tumor cell that has undergone or is capable of undergoing reversible adaptive plasticity. In other cases, the modified cell may be obtained from a tumor, neoplastic or tumor cell that is an anchorage-dependent cell. A modified cell may be obtained from a cancer, neoplastic or tumor cell that that is self-sufficient in growth signaling, insensitive to an anti-growth signal, lacks apoptotic capacity, has limitless replicative potential, induces or sustains angiogenesis and/or is metastatic or capable of invading host tissue. Modified cells may be obtained from unmodified carcinoma, sarcoma, myeloma, leukemia, lymphoma or a mixed type cancer or tumor cells including, but not limited to, neuroblastoma, melanoma, rhabdo-myosarcoma (M9) rhabdoid tumor, or pancreatic adenocarcinoma cells. Advantageously, modified cells may be produced from aggressive or malignant or other high-risk kinds of tumor or cancer cells.

Cellular modification to knock-out or attenuate Id protein expression or activity may be obtained by various methods including by genetic modification of cells, physical treatment of cells, such as by exposure to X-ray or UV-irradiation, or by chemical treatment of cells. For example, a modified cell may be produced by genetically modifying a cell to attenuate or knock-out expression of one or more Id proteins or an unmodified cell may be treated with an antibody or antibodies or other ligand(s) which binds to an Id protein and inhibits or attenuates its expression or activity.

Cells may be modified to attenuate Id protein expression by exposure to particular drugs or pharmaceuticals such as statins, such as fluvastatin, retinoic acid and its derivatives, doxorubicin, and natural or synthetic cannabinoid drugs, such as cannabidiol.

A modified cell in the immunogenic composition may have one or more Id proteins knocked-out or otherwise attenuated compared to an unmodified cell of the same type. Representative Id proteins include Id1 (SEQ ID NO: 2 or 10), Id2 (SEQ ID NO: 4 or 12), Id3 (SEQ ID NO: 6 or 14), or Id4 (SEQ ID NO: 8 or 16) or a protein that has an amino acid sequence at least 95% identical to that of SEQ ID NO: 2, 4, 6, 8, 10, 12, 14, or 16.

The amount or activity of the Id protein can be reduced by attenuating or knocking down its cellular expression. Useful methods include, but are not limited to RNA silencing by sh-RNA (small hairpin RNA) silencing or by another mode of RNA interference, by inhibiting the expression of a gene encoding the Id protein, by contacting the Id protein or a cell expressing the Id protein with a ligand, by contacting the Id protein or a cell expressing the Id protein with a ligand that is an antibody or an antigen-binding fragment of an antibody, or by contacting the Id protein or a cell expressing the Id protein with a small organic molecule or drug. Optionally, a modified cell may be further treated, for example, by radiation, chemicals, or drugs to reduce its proliferative capacity, enhance its immunogenicity, reduce immune responses to non-cancer determinants of the cell, or to otherwise modify its immunological, pharmacokinetic or pharmacodynamics properties. A protein, drug, chemical or other agent that inhibits or down-regulates an immune response may be used for the checkpoint blockade, for example, Kyi, et al., FEBS Lett. (2014) describes checkpoint blocking antibodies and is incorporated by reference.

Another aspect of the invention is a method for inducing immunity to a cancer or tumor cell by administering a composition according to the invention containing a modified cell to a subject in need of treatment, such as a patient having a tumor or having cancer. A method according to the invention may involve contacting a modified tumor cell with the blood, leukocytes, T cells, B cells, NK-cells, macrophages, microglia, dendritic cells, or other immunocytes or antigen-presenting cells of a subject. For example, an immunogenic composition comprising a tumor cell modified to attenuate or inhibit the expression of activity of an Id protein may be contacted with a subject's blood, antigen-presenting cells, leukocytes, T or B lymphocytes, or isolated T-cells, including CD4$^+$ or CD8$^+$ T-cells, NKT cells, gamma-delta T-cells, or mucosa associated invariant T-cells.

The treatment may be performed in conjunction with the administration of an immune modulator, such as an antibody to a checkpoint protein, antibodies that bind to T-cells, or other immunomodulators, such as biological or pharmaceutical products that inhibit, modulate or stimulate T-cell responses or drugs or agents that knock-down or attenuate Id protein expression. For example, an immunogenic composition containing a modified tumor cell that expresses an attenuated amount of an Id protein may be administered in conjunction with an antibody to CTLA-4 that can bind to CTLA-4 on T-cells or in conjunction with an antibody to PD-L1 that can bind to PD-L1 on the modified tumor cells and block binding of PD-L1 to PD-1 on a cytotoxic T-cell. Other immunomodulators which may be incorporated into the immunogenic composition include antibodies or ligands that antagonize the binding of CTLA-4 to its natural ligands, such as B7-1 or B7-2 and antibodies or ligands that antagonize the binding of PD-L1 or PD-1 to their natural ligands.

The composition according to the invention may be administered to a subject at the same time as an immune modulator or before or after such an immune modulator is administered. It also can be formulated into the composition according to the invention containing modified cells. The composition of the invention and/or immunomodulators may be administered one time or periodically, for example, on a daily, weekly, biweekly, or monthly basis.

Another alternative method is to expose the cells, tissues or organs of a subject in need of treatment to the composition according to the invention and, optionally, to one or more immunomodulators such as antibodies to CTLA4 or PD-L1, ex vivo or in vitro. After treatment, such treated cells, tissues or organs can be replaced into a patient.

Another aspect of the invention involves a method for inhibiting tumorigenicity or proliferation of a cell, or for promoting its differentiation, comprising reducing the amount or activity of an Id protein in the cell. The Id protein may be Id1 (SEQ ID NO: 2 or 10) or a protein that comprises an amino acid sequence at least 95% identical to SEQ ID NO: 2 or 10; Id2 (SEQ ID NO: 4 or 12) or a protein that comprises an amino acid sequence at least 95% identical to SEQ ID NO: 4 or 12; Id3 (SEQ ID NO: 6 or 14) or a protein that comprises an amino acid sequence at least 95% identical to SEQ ID NO: 6 or 14; Id4 (SEQ ID NO: 8 or 16) or a protein that comprises an amino acid sequence at least 95% identical to SEQ ID NO: 8 or 16; or combinations thereof. The amount or activity of the Id protein can be reduced by attenuating or knocking down its expression by a cell, by sh-RNA (small hairpin RNA) silencing or by another mode of RNA interference, by inhibiting the expression of a gene encoding the Id protein, by contacting the Id protein with a ligand, by contacting the Id protein with a ligand that binds to it, such as a ligand that can enter a cell and bind to an Id protein or a ligand that is expressed with a cell. Antibodies, antibody fragments, modified antibodies, or intrabodies binding to Id proteins, soluble or non-membrane anchored forms of natural ligands binding to Id proteins or Id-protein binding portions of such ligands may be employed. In other embodiments, the amount or activity of the Id protein can be reduced by contacting the Id protein or a cell expressing the Id protein with a small organic molecule or drug. Such a method may employ a modified tumor, neoplastic or cancer cell, including anchorage-dependent or anchorage-independent tumor cells, and can be performed in vivo, ex vivo or in vitro.

BRIEF DESCRIPTION OF THE DRAWINGS

This patent application file contains at least one drawing executed in color. Copies of a patent or patent application publication with color drawing(s) will be provided by the Office upon request and payment of the necessary fee.

FIGS. 1A, 1B, 1C, 1D and 1E describe cellular and molecular characteristics of reversible adaptive plasticity in neuroblastoma. FIG. 1A: Mouse (Neuro2a) and human (SK-N-SH) neuroblastoma cells grown as AD and AI phenotypes. These phenotypes are promoted in vitro by presence of serum (AD) or EGF/FGF (AI). Cells are transformed under these conditions in about a week (AI to AD) and two weeks (AD to AI). FIG. 1B and FIG. 1C: Affymetrix array performed on AD and AI Neuro2a and SK-N-SH cells identified >1,000 differentially expressed genes (5% FDR, >1.5 fold change). In the heat map: red genes are up-regulated and blue genes are down-regulated in the comparison of AD and AI cell phenotypes (n=4). FIG. 1D: Protein analysis by western blotting revealed activation of proteins involved in anoikis resistance in the AI phenotypes thereby validating the gene array profiling data. These include integrins, Bcl2, Akt, FAK/Src and Erk. FIG. 1E: Protein analysis also revealed overexpression of Id2 and n-myc in AD phenotypes of Neuro2a and SK-N-SH cells.

FIG. 2A: anchorage dependent and anchorage independent phenotypes of mouse melanoma (B16) and rhabdo-myosarcoma (M9) and human rhabdoid tumor (BT-12, RT-peri) and pancreatic adenocarcinoma (Panc-1) cell lines. FIG. 2B: Western blot analysis of these cell lines demonstrates reversible adaptive plasticity as well as over-expression of Id2 in AD cells compared to AI.

FIG. 3 shows that T-cells infiltrate a mouse Neuro2a tumor. $CD4^+$ (first bar) and $CD8^+$ ($2^{nd}$ bar) T-cells were detected in Neuro2a mouse tumor microenvironment by flow cytometry. Mice bearing 5 mm wt Neuro2a tumor were subjected to Id2kd Neuro2a vaccination (2 doses, 7 days apart) in combination with CTLA4 antibody (3 doses, 3 days apart). Tumors were harvested as soon as they started to regress. Tumor infiltrating lymphocytes were gated by CD45 staining. Significant increases in $CD8^+$ T-cells were noted in the regressing tumors of the vaccinated (CTLA4+Id2-kd Neuro2a cells) mice when compared to the growing tumors of unvaccinated mice. Data represented as mean±SD (n=5). Vaccine: Id2-kd Neuro2a.

FIG. 4A: Right leg of AJ mice (n=10) when inoculated with $1\times10^6$ Id2-kd Neuro2a cells, 70% of mice remained tumor free. FIG. 4B: One million wt Neuro2a cells were injected into the left leg of the tumor-rejecting mice (n=7) and 85% remained tumor free. FIG. 4C: Id2-kd Neuro2a vaccine (2 doses) in combination with CTLA4 antibody (3 doses) eradicated 80% of established tumors. Each line in FIG. 4C represents individual mouse tumor growth. FIG. 4D: Bioluminescence imaging depicting the course of tumor regression in a representative vaccinated mouse.

FIGS. 5A and 5B show increased immune responses in the tumor rejecting mice. The spleens of the vaccinated mice (Id2-kd Neuro2a+CTLA4 antibody) which rejected tumors (see FIG. 4) were harvested and the splenocytes were subjected to different antigenic stimulation in vitro for 48 hours. CD3, wt Neuro2a, Id2-kd Neuro2a and surviving were used as antigenic stimulators. $CD8^+$ cells were detected using flow cytometry (FIG. 5A) and IFNγ levels detected by ELISA (FIG. 5B) were significantly upregulated in these mice when compared to naïve mice. No change in the numbers of $CD4^+$ cells were observed. Data represented as mean±SD (n=10). N2a, Neuro2a; vaccine: Id2-kd Neuro2a.

FIG. 6A: Sixty percent of mice (n=9/15) challenged (right leg) with Id2 knock-down Neuro2a (Id2-kd N2a) cells rejected tumor and survived tumor-free, whereas all mice challenged with either wild type Neuro2a (wtN2a, n=20) or scrambled shRNA lentivirus transfected Neuro2a (sc-shRNA-N2a, n=5) cells died from tumor burden. FIG. 6B: Tumor free survivors from FIG. 6A were rechallenged with wtN2a cells into their left leg 6 weeks after they cleared the tumor and 8 out of 9 mice were protected from tumor growth. FIG. 6C: SCID and nude mice grew tumors aggressively following inoculation with Id2kdN2a cells. FIG. 6D: Following inoculation of wtN2a cells in the right leg, Id2-kd N2a (n=10) and wtN2a (n=5) cells were vaccinated into the left leg of mice, 3 and 5 days later respectively. The wild type tumor growth on the right leg was delayed in Id2-kd N2a vaccinated mice when compared to control unvaccinated mice or wtN2a vaccinated mice.)

FIG. 7A: Schematic diagram of the prophylactic Neuro2a tumor models. Two models (0-day and 5-day) were tested, in which three doses of α-CTLA4 antibody were administered either days 0, 3, 6 or 5, 8, 11 following Id2-kd N2a cell inoculation into the right leg of the mice (n=5 for each model). FIGS. 7B and 7C: Tumor growth curves show that 60% of mice challenged with only Id2-kd N2a cells (no α-CTLA4) survived tumor free (FIG. 7B) and in the 0-day model (FIG. 7C) 40% of mice never grew tumor and another 40% cleared the tumor slowly and became tumor free. Graph depicts tumor growth in individual mice. The parenthesis indicates number of mice that survived tumor free. FIG. 7D: All mice in the 5-day model survived tumor free, in contrast to 80% in the 0-day model or 60% in the Id2-kd cells model. FIG. 7E: Six weeks after tumor clearance, the tumor-free mice from FIG. 7B (n=9) were re-challenged with wtN2a cells into their left leg and 100% were completely immunized against wild type tumor growth. Only 1 of 5 mice (20%) treated previously with anti-CTLA4 antibody alone survived tumor free after wtN2a challenge at 6 weeks.

FIG. 8A: Schematic diagram of the therapeutic vaccination. Two established tumor models, namely Neuro2a (wtN2a) and AgN2a were tested, where mice challenged with either wtN2a or AgN2a cells were subjected to a combination immunotherapy with Id2-kd N2a and α-CTLA4 antibody starting at day 6 after inoculation. Neuroblastoma tumors are normally visible (5 mm in diameter) in AJ mice by day 6. Tumor growth curves in individual mice of wtN2a (FIG. 8B) and AgN2a (FIG. 8C) cells show that the Id2-kd tumor cell vaccination combined with immune-modulation cures mice with established tumor. Parentheses indicate the number of mice that survived tumor free.

FIGS. 9A, 9B, 9C and 9D show tumor clearance and the effect of irradiation on tumor cell immunogenicity. FIG. 9A and FIG. 9B depict representative mouse from untreated and combination therapy group showing growing and shrinking tumor respectively. All bio-luminescent images were analyzed under the same scale. FIGS. 9C and 9D: Irradiated wild type Neuro2a (IR-wt N2a, n=5) and irradiated Id2 knock-down Neuro2a (IR-Id2-kd N2a, n=5) were compared as whole tumor cell vaccine antigen source in combination with α-CTLA-4 antibody against AgN2a (see FIG. 3A). IR-Id2-kd N2a vaccine was able to eradicate 60% of tumors in comparison to IR-wtN2a cells which had no effect on growth of the AgN2a tumors. All mice in FIG. 9C were sacrificed on day 20 due to large tumor burden. The parenthesis indicates number of mice that survived tumor free.

FIGS. 10A, 10B and 10C: T cell immunity required for tumor eradication following combination therapy. Mice were depleted of specific T cell subsets by systemic administration of antibodies against CD4, CD8 and NK cells and subjected to combined Id2-kd N2a cells and α-CTLA-4 antibody treatment strategy, see FIG. 8A.

FIG. 10A: In vivo depletion of $CD4^+$, $CD8^+$ and NK+ cells (n=5 for all groups) shows that the therapeutic effect of the combined treatment was completely abrogated by $CD8^+$ cell depletion. Mice lacking NK cells were for the most part able to reject their tumors following therapy. $CD4^+$ T cell depletion initially appeared to have minimal adverse effects on the therapeutic vaccine strategy, but after 4 weeks all mice in the CD4 depletion group developed delayed tumors.

FIG. 10B: All CD8$^+$ T cell depleted mice developed tumors at the site of Id2-kd N2a cell vaccination as well.

FIG. 10C: Cell infiltrates from the tumors of CD4 depleted mice were stained with anti-CD45-FITC, CD4-APC and FoxP3-PerCPCy5.5 antibodies to identify Treg cells; there was no evidence of Treg cell infiltrate in the late developing tumors from CD4 depleted mice. Purified Treg cells were used as positive control.

FIG. 11A: Representative flow cytometry plots showing CD4+ and CD8$^+$ T-cells in CD45+ splenocytes of naïve (n=5), tumor bearing (n=3) and tumor free (n=5) mice. FIG. 11B: Graphical representation of FIG. 11A indicating significant (** p=0.013) increase in CD8+ cells in the spleens of mice cleared of tumor. FIG. 11C: Splenocytes of mice that cleared tumor had enhanced IFNγ secretion following stimulation with CD3 (*p<0.02), wtN2a or Id2-kd N2a cells (*** p<0.0001). FIG. 11D: Remarkable increase in CD45+ cells detected in the shrinking tumor. FIGS. 11E and 11F: Tumor infiltrating lymphocytes (TIL) following vaccination were quantified and a massive infiltration of CD8$^+$ T-cells was detected in the shrinking tumors (n=5) as opposed to the growing tumors (* p<0.02). FIG. 11G: Chromium-51 release assay exhibited potent cytotoxic activity of CD8$^+$ TIL from shrinking tumor (n=3); whereas the TIL isolated from growing tumors (n=4) show no activity at all. Data presented as mean±S.D.

FIG. 12A: Representative flow cytometry plots showing CD4$^+$ and CD8$^+$ T-cell population in the neuroblastoma tumor lymphocytes. FIG. 12B: Graphical representation of (A) indicating a remarkable infiltration of CD8$^+$ T-cells in the two tumors associated with OMS (NB-OMS) as opposed to the other three neuroblastoma (NB) tumors that had minimal TIL.

FIGS. 13A, 13B, 13C and 13D illustrate the phenomenon of reversible adaptive plasticity.

FIG. 13A shows Neuro2a neuroblastoma cells grown as AD and AI phenotypes. AD phenotype was promoted in vitro by presence of serum or and AI phenotype by EGF/FGF.

FIG. 13B shows Id2 higher amount of Id2 protein was associated with the AD phenotype than with the AI phenotype. Affymetrix Array identified 1180 differentially expressed genes in the AD and AI Neuro2a cells (Id2 Expression was most notable: 20-fold higher in AD). Protein analysis verified overexpression of Id2 in AD phenotype.

FIG. 13C illustrates the interrelation of AD and AI phenotypes. Id2 is critical for driving reversible adaptive plasticity in which the AD phenotype (Id2$^+$) is proliferative, whereas the AI phenotype (Id2$^-$) is dormant.

FIG. 13D shows that the presence of both Id2$^+$ and Id2-cells in the same tumor section reinforce tumor heterogeneity.

FIG. 14A: Diagram of the therapeutic vaccine strategy. Two established tumor models, namely Neuro2a (wtN2a) and AgN2a were tested, where mice challenged with either wtN2a or AgN2a Cells were subjected to a combination immunotherapy with Id2-kd N2a and α-CTLA4 antibody starting at day 6 after inoculation. Neuroblastoma Tumors are normally visible (5 mm in diameter) in AJ Mice by day 6.

FIGS. 14B and 14C show tumor growth curves for wtN2a and AgN2a, respectively. The results show that the Id2kd tumor cell vaccination combined with immune modulation cures mice with established tumors. The parenthesis indicates number of mice that survived tumor free.

FIGS. 15A, 15B, 15C and 15D compare the features of growing and shrinking tumors.

FIG. 15A: Representative Flow cytometry plots showing CD4$^+$ and CD8$^+$ T-cells in CD45$^+$ splenocytes of naïve (n=5), tumor bearing (n=3) and tumor free (n=5) mice.

FIG. 15B: Graphical representation of (A) Indicating significant (**p 0.013) increase in CD8$^+$ Cells in the spleens of mice cleared of tumor.

FIG. 15C: Splenocytes of mice that cleared tumor had enhanced IFNγ secretion following stimulation with CD3 (*p<0.02), wtN2a or Id2-kd N2a cells (*** p<0.0001).

FIG. 15D: Remarkable increase in CD45$^+$ cells was detected in shrinking tumors.

FIGS. 15E and 15F: Tumor infiltrating lymphocytes (TIL) following vaccination were quantified and a massive infiltration of CD8$^+$ T-cells was detected in the shrinking tumors (n=5) as opposed to the growing tumors (*p<0.02).

FIG. 15G: Chromium-51 release assay exhibited potent cytotoxic activity of CD8$^+$ TIL from shrinking tumor (n=3); whereas the TIL isolated from growing tumors (n=4) show no activity at all. Data presented as mean±S.D.

FIGS. 16A, 16B and 16C provide gene array analysis results of PD-L1 expression on AgN2A cells.

FIG. 16A: Gene array analysis and flow cytometry was performed on N2a and AgN2a tumor cells to quantify expression of PD-L1. A 3.7-fold increase in PD-L1 expression was noted in WI N2A by gene array and confirmed by flow cytometry.

FIG. 16B: Description of vaccination protocol.

FIG. 16C: Mice were challenged with WT N2a (1×10$^6$) and once tumors were established, mice were vaccinated with various combinations of Id2-kd N2a cells, and CTLA4/PD-L1 blocking antibodies. Tumor eradication in vaccinated mice was detected by chemiluminescent imaging.

FIG. 17A shows tumor growth in different treatment groups following vaccination. FIG. 17B shows the average tumor size and FIG. 17C shows survival in different treatment groups.

DETAILED DESCRIPTION OF THE INVENTION

Figure 2A:
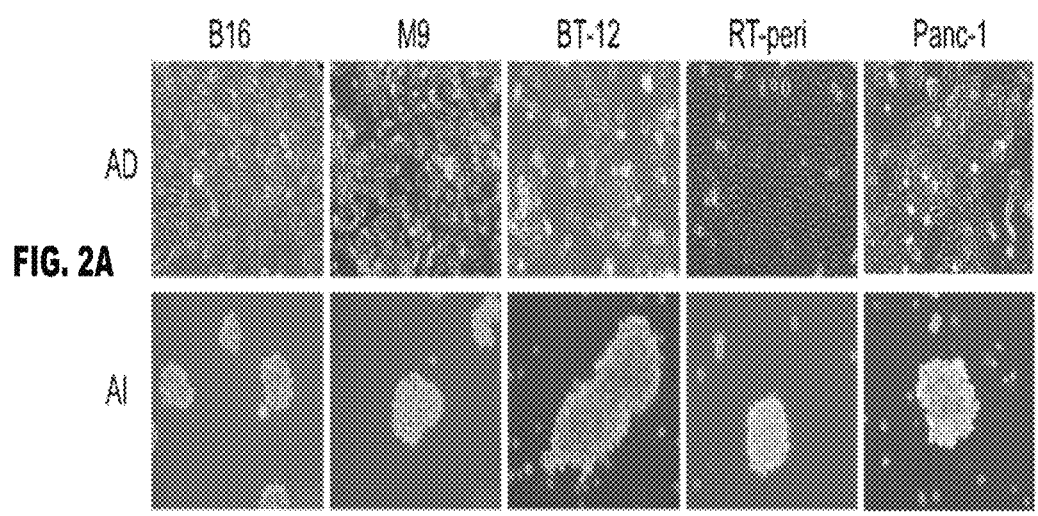
FIGS. 2A and 2B illustrate the reversible adaptive plasticity in various other tumor types.

AD phenotype refers to an anchorage dependent phenotype. AI phenotype refers to an anchorage independent phenotype. Examples of cells with AI and AD phenotypes are shown in FIG. 13A and FIG. 13B. As shown in FIG. 13B the AI phenotype is often associated with lowered expression of Id proteins. Anoikis is a form of programmed cell death which is induced by anchorage-dependent cells detaching from the surrounding extracellular matrix (ECM). Reversible Adaptive Plasticity ("RAP") enables a cell to transition between highly proliferative anchorage-dependent (AD) and slowly growing anoikis-resistant, anchorage-independent (AI) phenotypes.

B7 is a type of peripheral membrane protein found on activated antigen presenting cells (APC) that, when paired with either a CD28 or CD152 (CTLA-4) surface protein on a T cell, can produce a costimulatory signal or a coinhibitory signal to enhance or decrease the activity of a MHC-TCR signal between the APC and the T cell, respectively' Besides being present on activated APCs, B7 is also found on T-cells. Binding of the B7 on T-cells to CTLA-4 causes inhibition of the activity of T-cells. There are two major types of B7 proteins: B7-1 or CD80, and B7-2 or CD86. CD28 and CTLA-4 each interact with both B7-1 and B7-2.

CTLA4 or CTLA-4 (cytotoxic T-lymphocyte-associated protein 4), also known as CD152 (cluster of differentiation 152), is an immune checkpoint protein receptor that can downregulate the immune system. CTLA4 is found on the surface of T cells where it may act as "off" switch when bound to CD80 or CD86 on the surface of antigen-presenting cells.

A CTLA4 antagonist interferes or blocks a functionality of CTLA4, for example, it can block the ability of CTLA4 to down regulate T cell responses. Examples of such antagonists include antibodies that bind to CTLA-4 and inhibit or block its function, such as Ipilimumab (CAS number 477202-00-9). CTLA4 antagonists may be used in conjunction with the modified cells of the invention.

Gene Silencing is a method to prevent the expression of a gene, for example, by inhibiting transcription of a gene or the translation of mRNA transcribed from a gene. A silencing element can reduce or eliminate the expression level of the target sequence by influencing the level of the target RNA transcript or, alternatively, by influencing translation and thereby affecting the level of the encoded polypeptide. A single polynucleotide employed in the methods of the invention can comprise one or more silencing elements to the same or different target polynucleotides. Preferably, a silencing element has no significant effect on normal cells or tissues. Silencing elements can include, but are not limited to, a sense suppression element, an antisense suppression element, a double stranded RNA, a miRNA, or a hairpin suppression element. Non-limiting examples of silencing elements that can be employed to decrease expression of target Id protein nucleic acid sequences comprise fragments and variants of the sense or antisense sequence or consists of the sense or antisense sequence of the sequence set forth in SEQ ID NO: 1, 3, 5, 7, 9, 11, 13, and 15, including a gene or mRNA comprising these sequences or a biologically active variant or fragment thereof. A silencing element may contain chemical modifications to stabilize it in vitro or in vivo or to enhance its uptake by a cell containing a polynucleotide target, such as a polynucleotide encoding an Id protein.

A sense suppression element comprises a polynucleotide that expresses an RNA molecule corresponding to at least a part of a target messenger RNA in the "sense" orientation. Expression of the RNA molecule comprising the sense suppression element reduces or eliminates the level of the target polynucleotide or the polypeptide encoded thereby. The polynucleotide comprising the sense suppression element may correspond to all or part of the sequence of the target polynucleotide, all or part of the 5' and/or 3' untranslated region of the target polynucleotide, all or part of the coding sequence of the target polynucleotide, or all or part of both the coding sequence and the untranslated regions of the target polynucleotide. A sense suppression element may be at least 65%, 70%, 75%, 80%, 85%, 90%, 95%, or 99% identical to a portion of the target polynucleotide or may contain 1, 2, 3, 4, 5, 6, 7, 8, 9, 10, 15, 20 or more nucleotide deletions, substitutions or insertions to a corresponding sequence in a target polynucleotide. A sense suppression element may range in length from 10, 15, 16, 17, 18, 19, 20, 21, 22, 23, 24, 25, 30, 40, 50, 60, 70, 80, 90, 100, 200, 500 or more nucleotides. Sense suppression elements can be used to down-regulate, attenuate or eliminate the expression of Id proteins.

An antisense suppression element comprises a polynucleotide which expresses an RNA molecule complementary to all or part of a target messenger RNA. Expression of the antisense RNA suppression element reduces or eliminates the level of the target polynucleotide. The polynucleotide for use in antisense suppression may correspond to all or part of the complement of the sequence encoding the target polynucleotide, all or part of the complement of the 5' and/or 3' untranslated region of the target polynucleotide, all or part of the complement of the coding sequence of the target polynucleotide, or all or part of the complement of both the coding sequence and the untranslated regions of the target polynucleotide. In addition, the antisense suppression element may be fully complementary (i.e., 100% identical to the complement of the target sequence) or partially complementary (i.e., less than 100% identical to the complement of the target sequence) to the target polynucleotide. In specific embodiments, the antisense suppression element comprises at least 75%, 80%, 85%, 90%, 95%, or 99% sequence complementarity to the target polynucleotide. The antisense suppression element can be complementary to a portion of the target polynucleotide. An antisense suppression element is of sufficient length to bind to a target polynucleotide and inhibit is expression or other activity and may range in length from 10, 15, 16, 17, 18, 19, 20, 21, 22, 23, 24, 25, 30, 40, 50, 60, 70, 80, 90, 100, 200, 500 or more nucleotides. Antisense suppression elements may be used to down-regulate, attenuate or eliminate Id protein expression.

A double stranded RNA silencing element or "dsRNA" comprises at least one transcript that can form a dsRNA either before or after contact or absorption by a cell. A "dsRNA silencing element" includes a dsRNA, a transcript or polyribonucleotide capable of forming a dsRNA or more than one transcript or polyribonucleotide capable of forming a dsRNA. "Double stranded RNA" or "dsRNA" refers to a polyribonucleotide structure formed either by a single self-complementary RNA molecule or a polyribonucleotide structure formed by the expression of least two distinct RNA strands. The dsRNA molecule(s) employed in the methods and compositions of the invention mediate the reduction of expression of a target sequence, for example, by mediating RNA interference "RNAi" or gene silencing in a sequence-specific manner. The dsRNA can reduce or eliminate the level of or expression of a target polynucleotide or the polypeptide encoded thereby in a cell, such as a cell expressing an Id protein. In some embodiments, at least one strand of the duplex or double-stranded region of the dsRNA shares sufficient sequence identity or sequence complementarity to the target polynucleotide to allow for the dsRNA reducing the level of expression of the target sequence. As used herein, the strand that is complementary to the target polynucleotide is the "antisense strand" and the strand homologous to the target polynucleotide is the "sense strand." RNA silencing can be used to silence RNA encoding Id proteins.

In other embodiments, the dsRNA can comprise a small RNA (sRNA). sRNAs can comprise both micro RNA (miRNA) and short-interfering RNA (siRNA). miRNAs are regulatory agents comprising about 19 ribonucleotides which are highly efficient at inhibiting the expression of target polynucleotides. For miRNA interference, the silencing element can be designed to express a dsRNA molecule that forms a hairpin structure containing a 19-nucleotide sequence that is complementary to the target polynucleotide of interest. The miRNA can be synthetically made, or transcribed as a longer RNA which is subsequently cleaved to produce the active miRNA. Specifically, the miRNA can comprise 19 nucleotides of the sequence having homology to a target polynucleotide in sense orientation and 19 nucleotides of a corresponding antisense sequence that is complementary to the sense sequence.

When expressing a miRNA, it is recognized that various forms of a miRNA can be transcribed including, for example, the primary transcript (termed the "pri-miRNA") which is processed through various nucleolytic steps to a shorter precursor miRNA (termed the "pre-miRNA"); the pre-miRNA; or the final (mature) miRNA is present in a duplex, the two strands being referred to as the miRNA (the strand that will eventually base pair with the target) and miRNA*. The pre-miRNA is a substrate for a form of dicer that removes the miRNA/miRNA* duplex from the precursor, after which, similarly to siRNAs, the duplex can be taken into the RISC complex. It has been demonstrated that miRNAs can be transgenically expressed and be effective through expression of a precursor form, rather than the entire primary form The methods and compositions of the invention employ silencing elements that when transcribed "form" a dsRNA molecule. Accordingly, the heterologous polynucleotide, such as one encoding an Id protein, being expressed need not form the dsRNA by itself, but can interact with other sequences in a cell to allow the formation of the dsRNA.

Methods for gene silencing are incorporated by reference to Abdelrahim, et al., RNAi and cancer: Implications and applications, J RNAi Gene Silencing 2(1): 136-145 (2006). Methods using siRNA are incorporated by reference to Paddison, et al., Stable suppression of gene expression by RNAi in mammalian cells Proc Natl Acad Sci USA 99 (3): 1443-8 (2002) and to Whitehead, et al., Silencing or stimulation? siRNA delivery and the immune system. Annual Review of Chemical and Biomolecular Engineering 2: 77-96 (2011). The references cited above are incorporated by reference.

Id protein expression may also be knocked out or attenuated using CRISPR for targeted editing or regulation of genes encoding Id proteins, see Lei, et al., Cell 152(5): 1173-1183 (2013), Wang, et al., Cell 153 (4): 910-918. (2013), and Mali, et al., Science 339 (6121): 823-826 (2013) and which are incorporated by reference. The references cited above are incorporated by reference.

The term "Id protein" describes a family of proteins that inhibit DNA binding and also includes natural analogs or variants of Id proteins as well as engineered analogs or variants. Examples of human and murine Id proteins are described by SEQ ID NOS: 2, 4, 6, 8, 10, 12, 14 and 16. DNA and RNA encoding the Id proteins and natural analogs, engineered variants and modified forms is known in the art and may be easily deduced from an Id protein amino acid sequence using the genetic code. Nucleic acid fragments comprising all or a segment of an Id protein gene or structural gene are contemplated. Such fragments may comprise 5, 10, 15, 20, 25, 30, 35, 40, 45, 50, 100, 200 or more nucleotides. Antisense nucleic acids complementary to an Id protein nucleic acid or nucleic acid fragment may be produced and used to modulate Id protein expression, for example, by interference with transcription or translation of an Id protein. Modified nucleic acids with enhanced stability or modified biological half-lives are also contemplated including forms modified to affect the pharmacokinetic properties of a nucleic acid including its liberation, absorption (including cellular uptake), distribution, metabolization or excretion. Vectors may comprise such nucleic acids and host cells transformed or transfected with such nucleic acids or vectors are specifically contemplated.

Representative Id nucleic acid and amino acid sequences are shown in the table below. These sequences are also incorporated by references to the accession numbers shown below.

|  | Nucleic Acid | SEQ ID NO: | Amino acid | SEQ ID NO: |
| --- | --- | --- | --- | --- |
| Murine |  |  |  |  |
| Id1 | NM_010495.3 | 1 | NP_034625.1 | 2 |
| Id2 | NM_010496.3 | 3 | NP_034626.1 | 4 |
| Id3 | NM_008321.2 | 5 | NP_032347.1 | 6 |
| Id4 | NM_031166.2 | 7 | NP_112443.1 | 8 |
| Homo sapiens |  |  |  |  |
| Id1 | X77956.1 | 9 | CAA54920.1 | 10 |
| Id2 | NM_002166.4 | 11 | NP_002157.2 | 12 |
| Id3 | X73428.1 | 13 | CAA51827.1 | 14 |
| Id4 | NM_001546.3 | 15 | NP_001537.1 | 16 |

Natural analogs, allelic variants, engineered variants and modified forms of an Id protein or a nucleic acid encoding an Id protein are contemplated. Such analogs, variants and modified forms may have amino acid or polynucleotide sequences that are at least 70%, 85%, 90%, 95%, 96%, 97%, 98% or 99% identical or similar to a murine or human Id proteins or nucleic acids identified herein by accession number.

BLASTP can be used to identify an amino acid sequence having at least 70%, 75%, 80%, 85%, 87.5%, 90%, 92.5%, 95%, 97.5%, 98%, or 99% sequence identity or similarity to a reference amino acid using a similarity matrix such as BLOSUM45, BLOSUM62 or BLOSUM80. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. Polypeptides comprising portion or fragments of the amino acid sequence of SEQ ID NO: 2, 4, 6, 8, 10, 12, 14 or 16 or analogs, variants or modified forms thereof are also contemplated. The variants, portions or fragments of the amino acid sequence of SEQ ID NO: 2, 4, 6, 8, 10, 12, 14 or 16 preferably share at least one functional activity of a known Id protein.

Analogs, variants and modified forms of an Id protein can be produced by techniques well-known in the molecular biological, biochemical and chemical arts. For example, they can be made by expression of a polynucleotide or gene encoding these products in a suitable host cell or other techniques described by and incorporated by reference to Green & Sambrook, *Molecular Cloning: A Laboratory Manual*, Fourth Edition (2012). A DNA construct or expression vector for this purpose may be produced by conventional recombinant DNA techniques, such as by site-directed mutagenesis a sequence encoding an Id protein sequence described herein.

Polynucleotide sequences that encode Id proteins and Id protein analogs or variants or fragments thereof are described by reverse translating the protein sequence using the genetic code. Such polynucleotides may be isolated from natural sources, made by conventional recombinant DNA techniques, or by chemically synthesized. Nucleic acid constructs, vectors and host cells comprising Id polynucleotide sequences and their fragments may be produced by conventional recombinant DNA or RNA techniques, such as those described by Green & Sambrook, Molecular Cloning: A Laboratory Manual (Fourth Edition): Three-volume set 4th Edition (2012) or Rio, et al., RNA: A Laboratory Manual 1st Edition (2012) which are incorporated by reference.

BLASTN can be used to identify a polynucleotide sequence having at least 70%, 75%, 80%, 85%, 87.5%, 90%, 92.5%, 95%, 97.5%, 98%, or 99% sequence identity to a reference polynucleotide, such as a polynucleotide of SEQ ID NO: 1, 3, 5, 7, 9, 11, 13 or 15. A representative BLASTN setting optimized to find highly similar sequences uses an Expect Threshold of 10 and a Wordsize of 28, max matches in query range of 0, match/mismatch scores of 1/−2, and linear gap cost. Low complexity regions may be filtered/masked. Default settings are incorporated by reference to http://blast.ncbi.nlm.nih.gov/Blast.cgi?PROGRAM=blastn&BLAST_PROGRAMS=megaBlast&PAGE_TYPE=BlastSearch&SHOW_DEFAULTS=on&LINK_LOCblasthome (last accessed Dec. 24, 2015). Complements of the polynucleotides may also be easily produced based on the known complementarity of nucleotides and deoxynucleotides, for example, for the purpose of designing a polynucleotide that can specifically bind to a polynucleotide encoding an ID protein or to a portion of the regulatory polynucleotides sequences associated with expression of an ID protein.

Nucleic acids encoding Id polypeptides, polypeptide fragments, analogs, variants or modified forms of Id polypeptides may be incorporated into vectors or DNA constructs, such as into expression vectors that express an Id protein when transformed into a cell. Alternatively, such products may be produced in whole or part chemical synthesis such as by a Merrifield-type synthesis. Chemical synthesis is preferred for variants or modified forms that contain non-naturally-occurring amino acids. Modified forms may also comprise additional moieties, such as carrier or adjuvant moieties that alter the immunogenicity of an Id protein or chemical moieties that modify its pharmacodynamics or its pharmacokinetic properties including liberation, absorption, distribution, metabolization or excretion. The functional activities of such engineered products can be tested or screened for Id protein functionality by methods known in the art.

Immunomodulators useful in cancer immunotherapy are described by and incorporated by reference to the following publications: Blank, C. U., The perspective of immunotherapy: new molecules and new mechanisms of action in immune modulation. Curr Opin Oncol. 2014 March; 26(2): 204-14; Kyi, et al., Checkpoint blocking antibodies in cancer immunotherapy. FEBS Lett. 2014 Jan. 21; 588(2):368-76; and Naidoo, et al., Immune modulation for cancer therapy. Br J Cancer. (2014). Depending on the type of patient and tumor, those of skill in the art would select an appropriate immunomodulator for combination with an Id-protein-based therapy.

Programmed cell death protein 1, also known as PD-1 and CD279 (cluster of differentiation 279), is a protein that in humans is encoded by the PDCD1 gene. PD-1 is a cell surface receptor that belongs to the immunoglobulin superfamily and is expressed on T cells and pro-B cells. PD-1 binds two ligands, PD-L1 and PD-L2. The activity of PD-1 may be modulated by the binding of an antibody or other ligands to PD-1 or to its corresponding ligands.

Programmed death-ligand 1 (PD-L1) also known as cluster of differentiation 274 (CD274) or B7 homolog 1 (B7-H1) is a protein that in humans is encoded by the CD274 gene Programmed death-ligand 1 (PD-L1) is a 40 kDa type 1 transmembrane protein that has been speculated to play a major role in suppressing the immune system during particular events such as pregnancy, tissue allografts, autoimmune disease and other disease states such as hepatitis. Normally the immune system reacts to foreign antigens where there is some accumulation in the lymph nodes or spleen which triggers a proliferation of antigen-specific $CD8^+$ T cell. The formation of PD-1 receptor/PD-L1 or B7.1 receptor/PD-L1 ligand complex transmits an inhibitory signal which reduces the proliferation of these $CD8^+$ T cells at the lymph nodes. PD-1 is also able to control the accumulation of foreign antigen specific T cells in the lymph nodes through apoptosis which is further mediated by a lower regulation of the Bcl-2 gene.

The invention includes pharmaceutical preparations for humans and animals containing cancer, neoplastic or tumor cells modified to knock-out or attenuate Id protein expression or activity. For administration, the modified cancer, neoplastic or tumor cells can be combined with a pharmaceutically acceptable carrier such as a suitable liquid vehicle or excipient and an optional auxiliary additive or additives. The liquid vehicles and excipients are conventional and are commercially available. Illustrative thereof are distilled water, physiological saline, aqueous solutions of dextrose and the like. Suitable formulations for parenteral, subcutaneous, intradermal, intramuscular, oral or intraperitoneal administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, include for example, sodium carboxymethyl cellulose, sorbitol and/or dextran, optionally the suspension may also contain stabilizers. Also, the modified cancer, neoplastic or tumor cells can be mixed with immune adjuvants well known in the art such as Freund's complete adjuvant, inorganic salts such as zinc chloride, calcium phosphate, aluminum hydroxide, aluminum phosphate, saponins, polymers, lipids or lipid fractions, Lipid A, monophosphoryl lipid A, modified oligonucleotides, etc.

Radiation or irradiation includes, but is not limited to, photonic (e.g., X-ray or gamma ray), electron beam, and proton beam radiation. A target may be exposed to an external source or contacted with a radio-isotope in chemical form. Radiation enhancers may be used in conjunction with single or multiple dose radiation treatments.

Those skilled in the medical arts will readily appreciate that the doses and administration schedules of a pharmaceutical composition, such as the composition according to the invention containing modified cells, or other therapy, such as radiation treatment, will vary depending on the age, health, sex, size and weight of the human and animal. These parameters can be determined for each system by well-established procedures and analysis.

Reducing the amount of or the expression level of an Id polynucleotide or an Id polypeptide encoded thereby means that the levels of a polynucleotide or polypeptide target sequence is statistically lower than the polynucleotide level (e.g., mRNA) or polypeptide level of the same target sequence in a control cell which is not exposed to the silencing element. The expression level of a target polynucleotide (e.g., RNA) or the amount of a protein expressed may be reduced to 95%, 90%, 80%, 75%, 70%, 70%, 65%, 60%, 50%, 45%, 40%, 35%, 30%, 25%, 20%, 15%, 10%, 5% or less compared to the level in a control cell.

A target sequence or target polynucleotide is a sequence or polynucleotide selected for modulation, for example, to attenuate its transcription or translation or to otherwise affect or disrupt its function, particularly functions involving the expression of an Id protein. In some embodiments, the level of the target sequence in a cell will be reduced, in others its ability to be transcribed or translated into an Id protein can be reduced. A target sequence can be present in genomic DNA, in mRNA expressing an Id protein, such as the murine or human Id1, Id2, Id3 or Id4 proteins, or in a polynucleotide containing regulatory sequences affecting or controlling the expression of an Id protein.

A tumor cell vaccine according to the invention includes vaccines that reduce the severity of an existing cancer or prevent its progression or metastasis, as well as prophylactic vaccines that reduce the risk of getting cancer. Therapeutics that prime, induce antigen-specific memory, or otherwise condition the immune system to recognize a cancer are included. A tumor cell vaccine may contain autologous, allogeneic, xenogeneic or gene-modified tumor cells.

Tumor cell vaccine components include whole tumor cells that have been treated to attenuate, knock-down, or knock-out Id protein expression or the amount of Id protein in a tumor cell compared to an untreated tumor cell. Whole cells or fractions of cells, such as a membrane or cytoplasmic fraction may be used as immunogens, vaccines or immune modulators.

Example 1

The Role of Id Proteins in Reversible Adaptive Plasticity

Using a neuroblastoma model the inventors have described a new paradigm in tumor biology known as reversible adaptive plasticity (RAP). RAP enables the cells to transition between highly proliferative anchorage-dependent (AD) and slowly growing anoikis-resistant, anchorage-independent (AI) phenotypes (FIG. 1A), see Chakrabarti, et al., Front. Oncol. 2:82 (2012) which is incorporated by reference. The cells undergo this transition during tumor growth in vivo and the inventors have associated this transition with the altered expression of Id proteins.

In an effort to investigate the molecular footprint and mechanism(s) driving reversible phenotypic transition, the gene expression profiles and signaling pathways activated in the AD and AI phenotypes of mouse and human neuroblastoma cell lines were investigated. In agreement with their cellular characteristics, AD cells showed increased levels of proliferation-promoting molecules like inhibitors of differentiation proteins (Id) and n-myc (FIG. 1B, 1C, 1E). The AI cells, on the other hand, displayed activation of anoikis-resistant, tyrosine kinase pathways (Erk, FAK, Src and Akt), as well as overexpression of integrins (FIG. 1F); Chakrabarti, et al., PLOS One 8:e83521 (2013). Thus, AD and AI phenotypes display distinct cellular and molecular characteristics.

Id proteins disrupt the antiproliferative effects of retinoblastoma (Rb) family tumor suppressor proteins thus allowing cell cycle progression; Iavarone, et al., Genes Dev. 8:1270 (1994). Id is critical for cell proliferation and is the oncogenic effector of n-myc in human neuroblastoma; Lasorella, et al., Nature 407:592 (2000); Lasorella, et al., Cancer Res. 62:301 (2002). Id also mediates mitogenic signals, inhibits differentiation and plays a critical role in cancer development and metastasis; Kowanetz, et al., Mol. Cell Biol. 2:4241 (2004); Lasorella, et al., Mol. Cell biol. 25:3563 (20050; Ruzinova, et al., Trends Cell. Biol. 13:410 (2003). Due to these known functions and its remarkable differential expression in the cell phenotypes (Id2 is 20 fold overexpressed in Neuro2a AD compared to AI and Id1 and Id3 are 12 and 7 fold overexpressed in the SKNSH human AD cells respectively by Affymetrix gene array), we reasoned that Id2 could play a key role in reversible adaptive plasticity in the neuroblastoma cells. The inventors indeed found that forced down-regulation of Id2 in AD cells or overexpression in AI cells promoted characteristics of the opposite phenotype; Chakrabarti, et al., PLOS One 8:e83521 (2013). These findings led the inventors to explore whether blocking Id proteins would act as an inhibitor of proliferation or a negative regulator of the phenotypic transition from AD cells to AI cells.

To determine if phenotypic transformation is a generalized phenomenon for aggressive tumor cells, the inventors grew human rhabdoid tumor cell lines (BT-12, and RT-peri), human pancreatic adeno-carcinoma cell line (Panc-1), mouse melanoma (B16) and mouse rhabdomyosarcoma (M9) cell lines in AD medium with 10% serum or in serum free neural stem cell (AI) medium. They found that all the cell types were able to grow as AD and AI phenotypes demonstrating reversible adaptive plasticity as a novel phenomenon for many aggressive tumor types (FIGS. 2A and 2B).

Figure 2B:
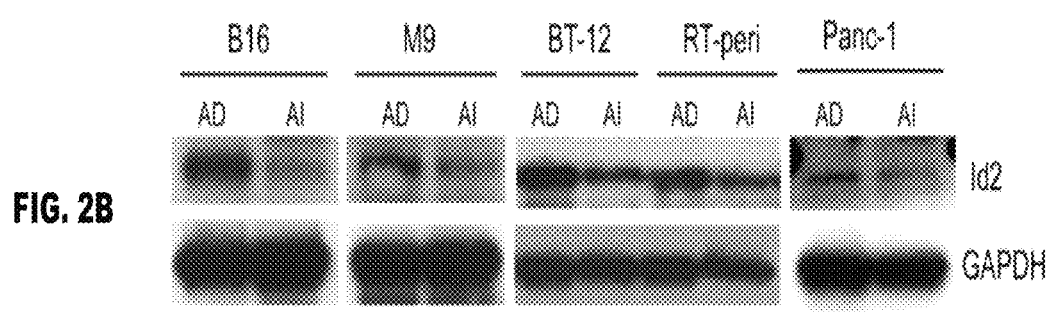

In favor of the potentially broad role that Id2 plays in other tumor types, Id2 was up-regulated in all AD cells of the lines tested when compared to AI phenotypes (FIGS. 2A and 2B). These new observations presented broad implications for many high-risk solid tumors that exhibit reversible adaptive plasticity and show that Id proteins may be a common and critical molecular switch for proliferation and phenotypic transition in aggressive tumors.

Figure 4A:
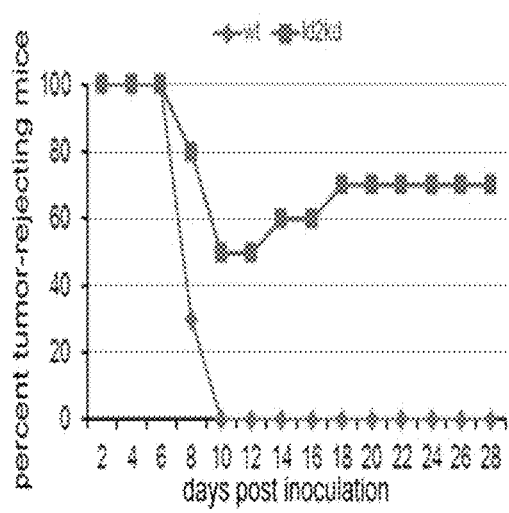
FIGS. 4A, 4B, 4C, and 4D show that Id2 knock-down attenuated neuroblastoma tumorigenicity.
Figure 4B:
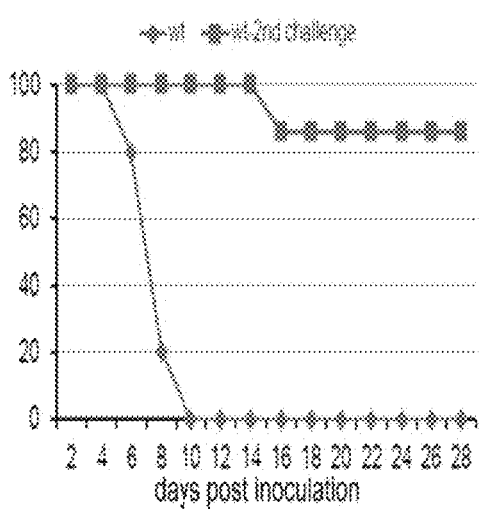

Targeting Id Proteins in Tumor Cells Renders the Cells Attenuated and Immunogenic and Rejection is Dependent on an Intact T-Cell Response In an attempt to determine the effect of knock-down of Id protein on tumorigenicity and adaptive transition, the inventors knocked down Id2 in Neuro2a cells with lentiviral-Id2shRNA and transduced cells were selected using puromycin. Implantation of Id2 knock-down neuro2a (Id2-kdN2a) cells in mice resulted in cell rejection in 70% of the mice (FIG. 4a) and these mice were subsequently protected against further wild-type tumor challenge (FIG. 4b). These findings suggest that down regulation of Id2 not only attenuated tumorigenicity in the mouse model, but also induced immunity against subsequent tumor challenge.

To further investigate if this was an immune mediated inhibitory mechanism, Severe Combined Immuno Deficient (SCID) mice (T cell, B cell, NK cell, dendritic cell and macrophage deficient) were challenged with Id2kd-N2a cells in parallel with wt Neuro2a (1×10⁶ cells each). Tumors developed in all mice, with wt and Id2kd tumors growing at the same rate. Additionally, when nude mice (T cell deficient) were challenged with 1×10⁶ Id2kd-N2a cells, all mice (100%) developed tumors at the site of Id2kd-N2a implantation. The inventors found that Id2kd-N2a cells stimulated a potent T cell mediated immune response as compared to wild type cells.

Next the inventors sought to increase the effectiveness of the immunotherapeutic strategy with the use of additional immunomodulatory agent(s) to enhance immunity. The immunomodulatory monoclonal antibodies generate effective antitumor immunity by enhancing endogenous T-cell responses through targeting key receptors in the immune system; Khalil, et al., Update Cancer Ther. 2:61-5 (2007), Peggs, et al., Clin. Exp. Immunol. 157:9-19 (2009), Weber, et al., Semin. Oncol. 37:430-7 (2010). The immunomodulators and techniques described by these references are incorporated by reference. In particular, blocking antibodies against CTLA4 were shown not only to augment antigen-specific T-cell responses, but also to provide therapeutic benefit in murine syngeneic tumor models; Brunner, et al., J. Immunol. 162:5813-20 (1999), Chambers, et al., PNAS USA 96:8603-8 (1999); Duraiswamy, et al., Cancer Res. 73:3591-603 (2013), Van Elsas, et al., J. Exp. Med. 190: 355-66 (1999) and Williams et al., Clin. Cancer Res. 19:3545-55 (2013). The immunomodulators and techniques described by these references are incorporated by reference. Anti-CTLA-4 antibody has been granted FDA approval and early phase studies have suggested potential benefit in a number of adult malignancies like melanoma and lymphoma; Ansell, et al., Clin. Canc. Res. 15:6446-53 (2009), Calabro, et al. Semin. Oncol. 37:460-7 (2010) and Hodi, et al., N. Engl. J. Med. 363:711-23 (2010). The immunomodulators and techniques described by these references are incorporated by reference.

Figure 3:
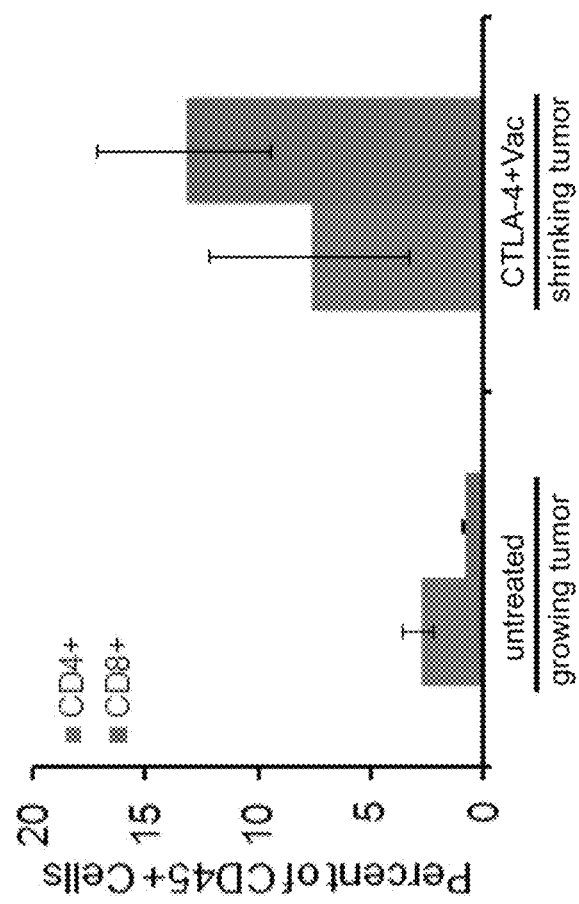
Figure 4C:
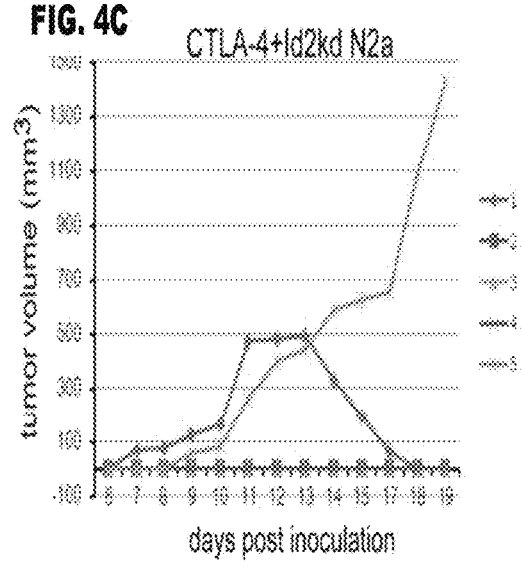
Figure 4D:
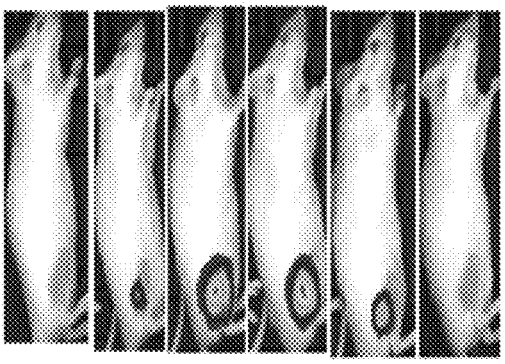
Figure 5A:
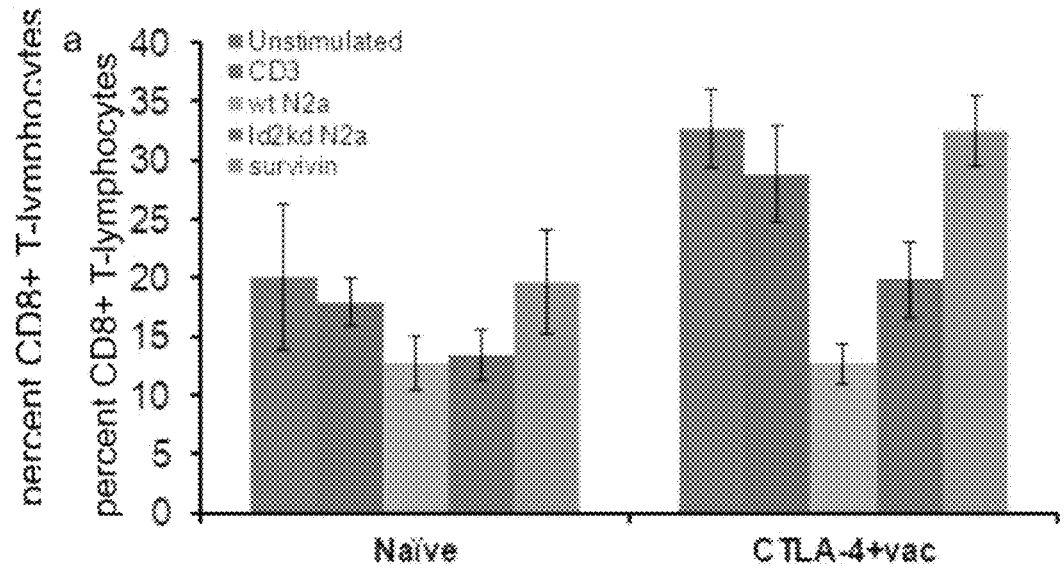
Figure 5B:
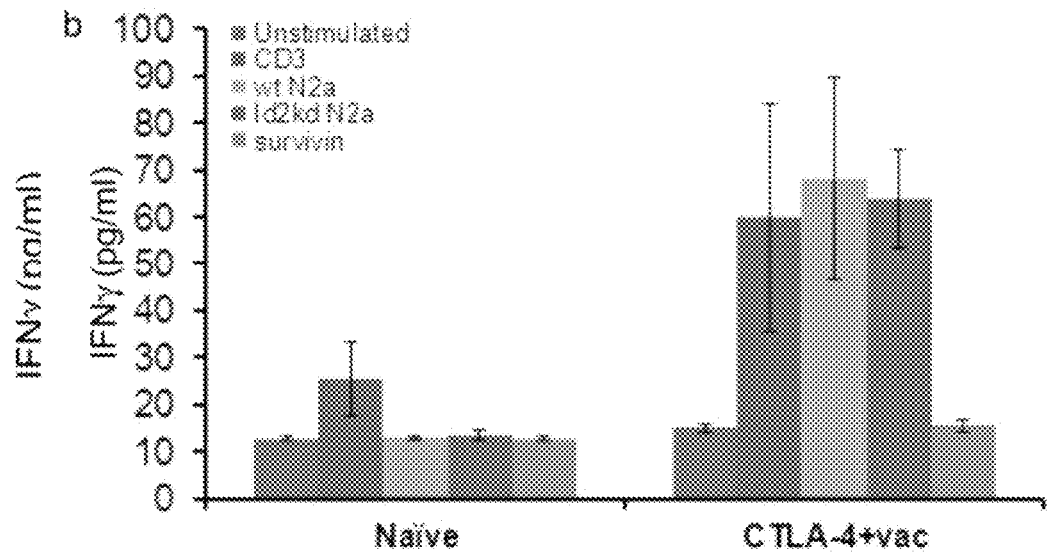

The inventors found that immunization using Id2kd-Neuro2a vaccine in combination with CTLA4 blockade induced eradication of large established neuroblastoma tumors (FIG. 4C, 4D). Moreover, when tumor microenvironment was analyzed for T-cell infiltrates, a high number of CD8 T-cells were found to infiltrate the shrinking tumor compared to growing tumors (FIG. 3) validating the role of T-cell immunity in this vaccine strategy. Furthermore, an increased number of CD8⁺ cells (FIG. 5A) and enhanced production of IFN-γ (FIG. 5B) were observed in the spleen cells (splenocytes) of the mice that were cured of tumor.

As shown above, an attenuated live tumor cell vaccine safely produces broad cellular tumor-specific immunity, protects against tumor formation in prophylactic tumor models and in combination with the clinically relevant immune modulator (CTLA4 antibody) cures mice with large established tumors.

Example 2

Effects of Id2 Knock-Down

The inventors recently described that targeting Id2 expression in anchorage dependent Neuro2a cells reduced their proliferation, increased the rate of tumorsphere formation and activated tyrosine kinase and TGFβ signaling pathways; Chakrabarti, et al., PLOS One 8:e83521. In an attempt to determine the effect of Id2 downregulation on Neuro2a tumorigenicity and adaptive transition in vivo, the inventors knocked down Id2 with lentiviral vectors expressing Id2 shRNA in neuro2a cells. The Id protein knock-down was confirmed by western blot analysis of Id2 protein expression.

The following materials are methods were used.

Animals: Female A/J, SCID and nude mice (6 weeks old) were purchased from Jackson Laboratory (Bar Harbor, Me.). The animals were acclimated for 4-5 days prior to tumor challenge. All procedures were approved by the Institutional Animal Care and Use Committee of Children's National Medical Center, Washington D.C.

Cells: Neuro2a is the murine neuroblastoma cell line derived from AJ mice and purchased from ATCC (Manassas, Va.). Cells were cultured as anchorage dependent in DMEM (Gibco, Carlsbad, Calif.) containing 10% fetal bovine serum (FBS, Gibco) and 1% penicillin/streptomycin (Sigma, St. Louis, Mo.). The aggressive subclone of Neuro2a (AgN2a) cells was produced by repeated in vivo passaging of the cells as described previously; Johnson, et al., Cell Immunol. 222:15-26.

Human neuroblastoma samples: De-identified fresh human neuroblastoma samples were obtained from the Pathology department of CNMC. Written informed consents were obtained from the parents or guardians of the patients in accordance with the Declaration of Helsinki. All procedures involving the use of human tumor specimens were approved by the Institutional Review Board of CNMC.

Cell transductions: The anchorage dependent Neuro2a cells were transduced with Id2-shRNA expressing lentiviral particles containing a Puromycin resistance gene (Santa Cruz Biotechnology, Santa Cruz, Calif.) for stable knockdown of Id2. The stable clones expressing the Id2-shRNA (Id2kd N2a) were selected using Puromycin according to the manufacturer's instructions. Scrambled shRNA lentiviral particles were used as control and effective transfection of scrambled sh-RNA again was proven with Puromycin selection similar to the Id2-kd clones. Untransfected controls did not survive the Puromycin challenge. The knock-down of Id2 was validated by western blot analysis. Luciferase expressing Neuro2a cells were constructed by transducing the Neuro2a cells with luciferase (firefly) expressing lentiviral particles (GenTarget Inc, San Diego, Calif.) and selecting the clones with Puromycin. Luciferase expression was determined by measuring bioluminescence in a luminometer using the Luciferase Assay System (Promega, Madison, Wis.). Antibodies Anti-CTLA-4 antibody (9D9) and mouse IgG2b isotype control were purchased from BioXCell. Anti-rabbit Id2 antibody was purchased from Santa Cruz Biotechnology. Mouse anti-CD4-APC, CD8α-PercP, CD45-FITC, purified mouse anti-CD8α, CD4, NK1.1 and CD3 antibodies and mouse regulatory T cell staining kits were purchased from eBioscience (San Diego, Calif.).

Mouse neuroblastoma therapy models: The right flank of A/J mice were injected subcutaneously (s.c) with 1×10⁶ freshly prepared tumor (Neuro2a or AgN2a) cells in 100 µl PBS on day 0. One million Id2-kd N2a cells were injected (s.c.) on their left flank on day 6 and again on day 13. The mice developed 5 mm size tumors on their right flank by day 6. Anti-CTLA-4 antibody (150 µg per mouse) or equivalent amount of IgG2b isotype control were administered intraperitoneally (i.p.) on days 6, 9 and 12. Mice were monitored daily following tumor inoculation. Tumor growth was recorded on alternate days by measuring the diameter in two dimensions using a caliper and by imaging the mice for tumor bioluminescence using IVIS Lumina III (Perkin Elmer). Tumor volume was calculated using the formula: (large diameter×small diameter) 2×0.52. A tumor size of 20 mm diameter in any dimension was designated as the endpoint and mice were euthanized at that time. Euthanasia was achieved through cervical dislocation after $CO_2$ narcosis. If the tumor impaired mobility of the animal, became ulcerated or appeared infected, or the mice displayed signs of "sick mouse posture" the mice were euthanized and removed from the study group. Food was provided on the cage floor when the tumor size reached 15 mm in diameter. All the procedures are approved by the IACUC at CNMC and are in accordance with the humane care of research animals. In vivo T cell depletion models CD8/CD4/natural killer (NK) cells were depleted by i.p. administration of purified anti-CD8α (100 μg/mouse), CD4 (100 μg/mouse) and NK1.1 (300 μg/mouse) depletion antibodies starting a day prior to Neuro2a cell inoculation and by repeating injections on days 3, 7, and 11 after inoculation. Depletion of $CD8^+$, $CD4^+$ and $NK1.1^+$ T-cells were validated using peripheral blood and analyzed by flow cytometry (>95% depletion). All the mice in depletion studies were subjected to Id2-kd N2a cell vaccination and CTLA4 blockade as described above.

Tumor digestion: Mouse and human tumors were weighed, and minced in 2 mL of serum free RPMI. Minced tumors were placed in a 50 mL tube, and filled to a final volume of 5 mL serum free RPMI per 1 g of tumor. Enzymatic digestion of tumors were performed with Collagenase I (Sigma), Dispase II (Roche) and DNase I (Roche) used at a final concentration of 1,500 U/mL, 4.8 mg/mL, and 3,000 U/mL, respectively. The tumors were digested in a 37° C. shaker bath for 20 minutes, and then placed on ice for 1-2 minutes, allowing the remaining undigested pellet to settle. The supernatant containing the single cell suspension was passed through a 40 μm strainer, before being centrifuged at 250×g for 5 minutes, and finally resuspended at the desired volume.

Flow cytometry: Cells from mouse and human tumor digests and splenocytes were stained for CD4, CD8 and CD45 using fluorochrome conjugated antibodies described above and flow cytometry was performed in a FACSCalibur (BD Biosciences, San Jose, Calif.). Data analysis was done using FlowJo software (Tree Star, Inc., Ashland, Oreg.).

Interferon-γ by ELISA: Spleen cells were harvested and $2\times10^5$ cells were plated per well into 96-well round-bottom plates. The spleen lymphocytes were stimulated with the following: $2\times10^4$ wild type Neuro2a cells, $2\times10^4$ Id2 knock-down Neuro2a cells and 1.0 μg/mL of purified anti-CD3. Splenocytes were then incubated at 37° C. for 48 hours prior to IFN-γ assay. Cell culture supernatants were collected from triplicate wells after stimulation and IFN-γ secreted by lymphocytes were measured by ELISA using purified capture and biotinylated detection antibody pairs (BD Biosciences). The ELISA plates were read using the EnSpire 2300 Multilabel Reader (Perkin Elmer, Shelton, Conn.) at 450 nm.

Chromium-51 release cytotoxicity assay: Cytotoxic T lymphocyte activity of tumor infiltrating lymphocytes was determined by standard 51 Cr release assays. In brief, Neuro2a cells (target) were incubated with 0.2 mCi Na[51] $CrO_4$ for 45 min at 37° C. Cells were washed twice with complete medium and transferred to round-bottom 96-well plates at $5\times10^3$ cells/well. $CD8^+$ T-cells (effector) were purified from the unvaccinated growing and vaccinated shrinking total tumor digest using the MACS cell separation system (Miltenyi Biotec, Auburn, Calif.). Due to low abundance of the infiltrating lymphocytes in the growing tumors, purified T-cells were pooled together from four unvaccinated growing tumors for the assay. Effector T-cells were added to target tumor cells at varying numbers in a final volume of 0.2 ml to give the effector:target ratios as indicated in the Figure legends. After 4 hours incubation at 37° C., 0.1 ml of supernatant was harvested, and released radiolabel was determined by scintillation counting. Maximal release from targets was determined by treatment of cells with 1% Triton X-100, spontaneous release was determined from cultures of labeled targets incubated with medium only, and the formula used for determination of specific lysis was: [(experimental release–spontaneous release)/(maximal release–spontaneous release)]×100. Statistical analysis The two-tailed Student's t-test was used to determine statistical significance between groups unless otherwise stated. A probability level of $p<0.05$ was considered to be statistically significant.

Figure 6A:
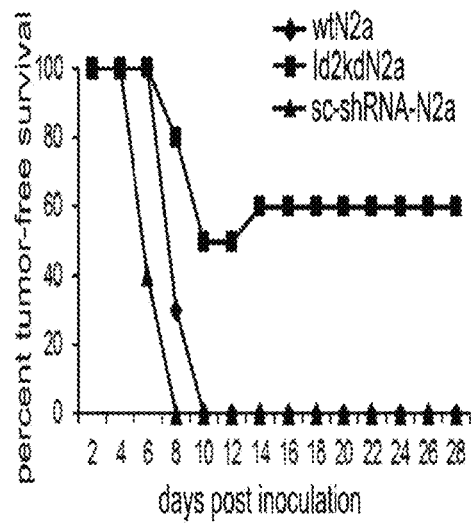
FIGS. 6A, 6B, 6C and 6D show that Id2 knock-down attenuated tumorigenicity and induces host immunity.
Figure 6B:
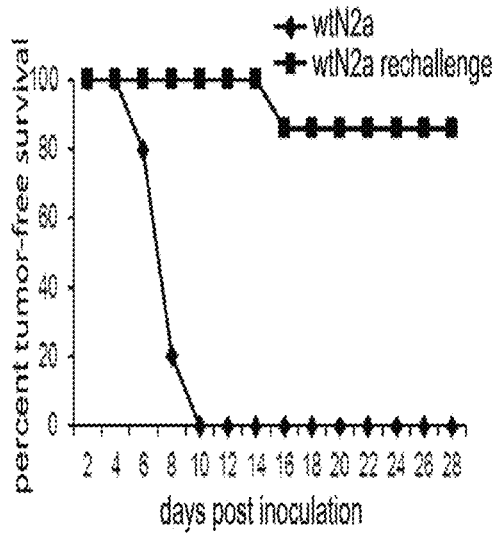
Figure 6C:
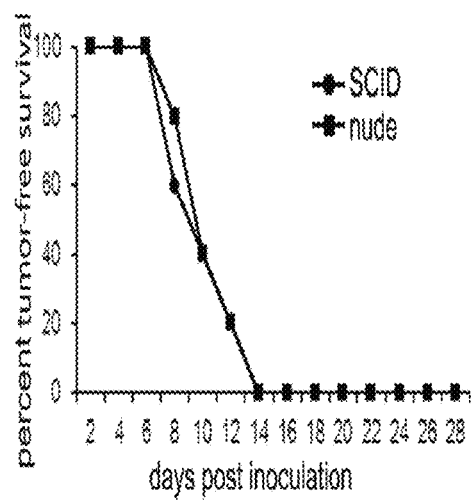
Figure 6D:
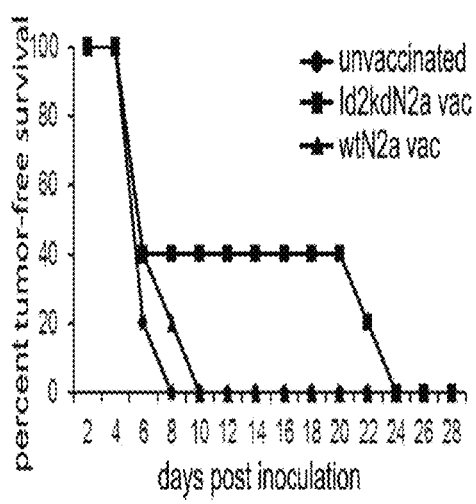

As shown above, the knock-down of inhibitor of differentiation protein 2 (Id2) attenuated neuroblastoma tumor cells and induced host immunity Implantation of Id2-kd N2a cells surprisingly resulted in tumor rejection in 60% of mice (FIGS. 6A and 6B) and these mice were subsequently protected against further wild-type Neuro2a tumor cell challenge (FIG. 6B). In contrast, severe combined immune-deficient (SCID) and nude mice grew Id2-kd tumors aggressively (FIG. 6C), highlighting the immunogenicity of the Id2-kd cells. The tumorigenicity of scrambled shRNA lentivirus transfected Neuro2a cells (sc-shRNA-N2a) was comparable to the wild-type cells (FIG. 6A). These findings suggested that down regulation of Id2 not only attenuates tumorigenicity in the mouse model, but also induced host immunity indicating the potential role of Id2-kd N2a cells as an antigenic vehicle for an attenuated, whole tumor cell vaccine. To this end, the inventors tested the use of Id2-kd N2a cells in a therapeutic treatment model of established neuroblastoma tumor. Id2-kd N2a cells were vaccinated into the left leg of mice, three days following inoculation of wild type Neuro2a tumor cells in the right leg, and tumor growth was monitored. None of the mice developed tumor at the site of Id2-kd N2a cell injection, while the growth of wild type tumor on the opposite leg was delayed when compared to control unvaccinated mice (FIG. 6D). In contrast, when wild type cells were injected into both hind legs 5 days apart, tumors grew aggressively on both sides, suggesting the absence of concomitant immunity in the wild type Neuro2a, validating the immunogenicity and potential use of Id2-kd N2a cells as a tumor vaccine.

Figure 7A:
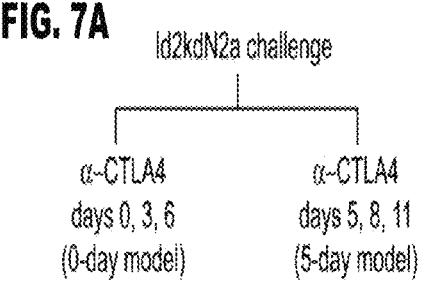
FIGS. 7A, 7B, 7C, 7D and 7E: CTLA-4 antibody enhances anti-tumor effect of Id2-kd N2a cell vaccine in prophylactic tumor models.
Figure 7B:
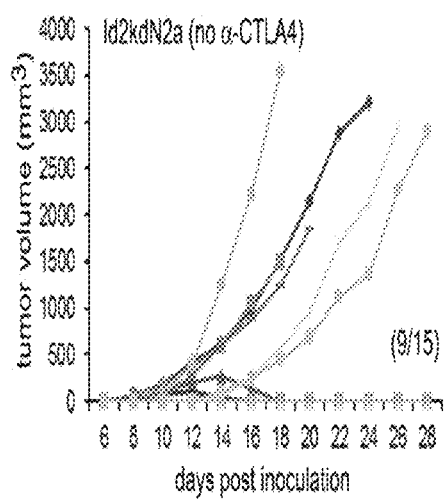
Figure 7C:
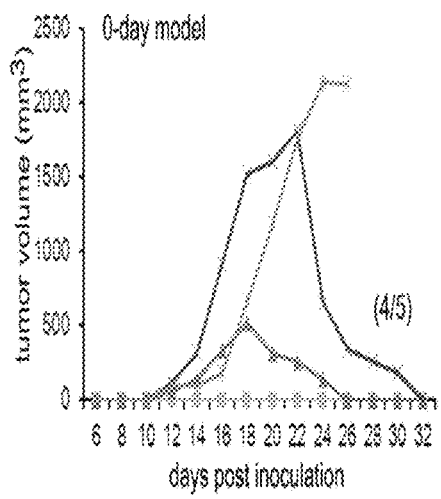
Figure 7D:
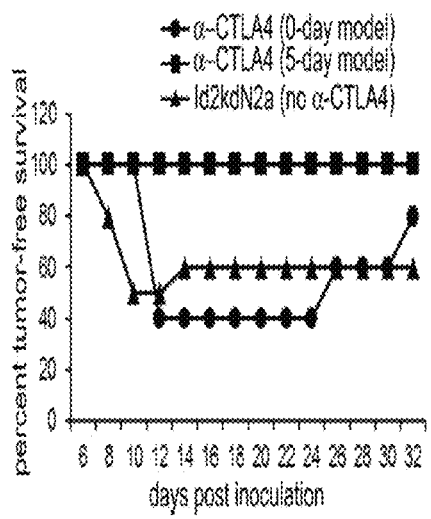
Figure 7E:
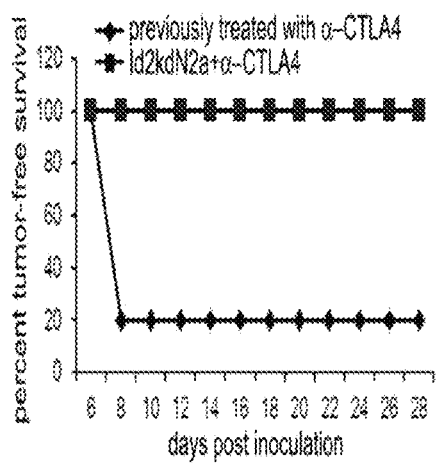

CTLA-4 Blockade Enhanced Anti-Tumor Immunity Induced by Id2 Knock Down Neuroblastoma Cells In order to determine if the therapeutic effect of the Id2-kd N2a whole tumor cell vaccine could be enhanced, the inventors combined this therapy with immune checkpoint blockade in the form of anti-cytotoxic T lymphocyte associated antigen 4 (CTLA-4) antibodies. Indeed, in a prophylactic tumor vaccination model (FIG. 7A) we observed that CTLA-4 blockade started on day 5 after Id2-kd N2a cell implantation resulted in 100% tumor rejection (FIG. 7D) in contrast to 80% when given on the same day as the Id2-kd N2a cells (FIGS. 7C and 7D) highlighting the synergy between immune priming and immune modulation that is required for effective tumor vaccine therapy. Moreover, all tumor-rejected mice developed complete immunity against wild type tumor cells challenged 6 weeks after tumor clearance (FIG. 7E).

Figure 8A:
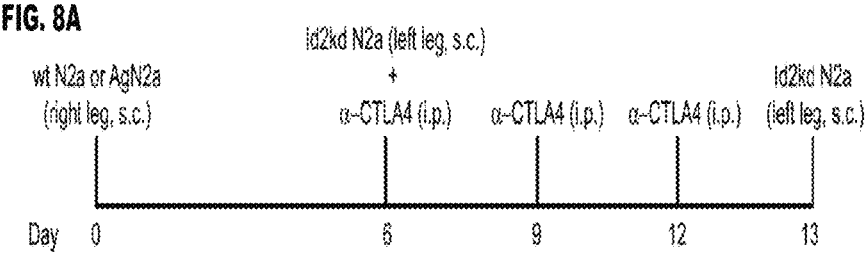
FIGS. 8A, 8B and 8C show the combination of Id2-kd N2a and α-CTLA4 antibody as a therapeutic vaccine.

Encouraged by the effectiveness of this prophylactic model, the inventors reasoned that the combination of the Id2-kd N2a vaccine platform with anti-CTLA-4 antibody may break tolerance even in the presence of large established tumors and induce potent T-cell immunity. The combined vaccine/immunotherapy effect in an established neuroblastoma tumor model was examined (FIG. 8A).

Figure 8B:
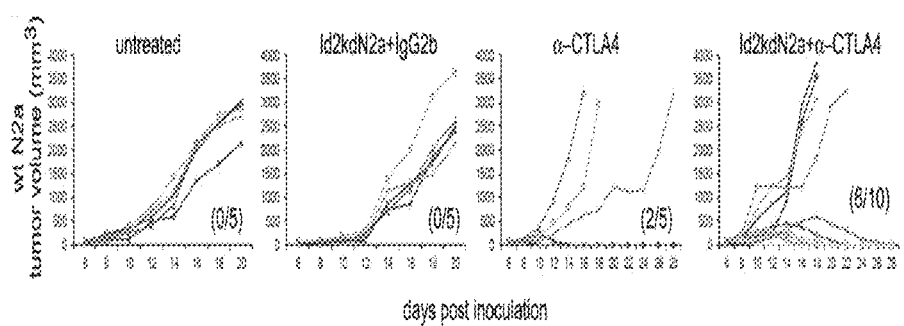
Figure 8C:
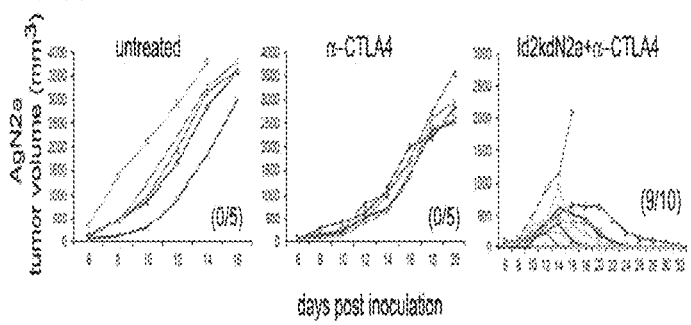

Combined therapy eradicated 60% of established Neuro2a tumors in the wildtype model (FIG. 8B) and 90% in AgN2a (aggressive non-immunogenic) model (FIGS. 8C, 9A and 9B), whereas, CTLA-4 blockade alone resulted in 40% tumor regression in the Neuro2a model and had no effect on tumor growth in the AgN2a model (FIGS. 8B and 8C). Of interest, again none of the mice developed tumor at the site of Id2-kd N2a cell injection in this established tumor model.

Irradiation of Id2-kd N2a Whole Tumor Cells Did not Impair Immunogenicity

Live attenuated vaccines induce long-lived cellular and humoral immunity, but safety concerns limit their utilization. Inactivation and attenuation of pathogens have been strategies for vaccine development since the advent of vaccination; Plotkin et al., Nat. med. 11:S5-11 (2005). Therefore, in lieu of the potential risk of live albeit attenuated Id2-kd N2a tumor cells the inventors sought to determine whether irradiation of these cells would dampen the effects of this tumor cell vaccine strategy. The inventors subsequently tested irradiated (35 Gray) Id2-kd N2a cells as a whole tumor cell vaccine antigen source in combination with anti-CTLA-4 antibody against AgN2a (FIG. 8A) and found that 60% of mice eradicated established tumors (FIG. 9D). In contrast, irradiated wild type Neuro2a cells administered in a similar combination fashion, had no effect on growth of the AgN2a aggressive tumor cells (FIG. 9C). This observation again supports the antigenicity of Id2-kd N2a cells for vaccination, but is also encouraging in that irradiation extends the margin of vaccine safety.

Although irradiation of tumor cell vaccines is known to evoke potent anti-tumor immunity in melanoma and lung cancer models; Salgia, et al., J. Clin. Oncol. 21:624-630 (2003); Dranoff, et al., PNAS USA 90:3539-3543 (1993), it was found that neither a favorable nor particularly adverse effect of irradiation on the antigenic properties of the Id2-kd cells in neuroblastoma. Taken together these results suggest that Id2-kd N2a cells would provide a safe and effective source of tumor antigenicity and in combination with checkpoint blockade induce potent tumor immunity.

$CD8^+$ T-Cells were Necessary and $CD4^+$ T-Cells were Required for Neuroblastoma Tumor Eradication To explore which immune effector cells are critical for eradicating the established tumors following combined vaccine therapy, the inventors depleted specific T cell subsets by systemic administration of antibodies against CD4, CD8 and Natural Killer (NK) cells. In vivo depletion of cell phenotypes was confirmed by blood sampling. Depletion of $CD8^+$ T-cells completely abrogated the therapeutic effect of combined Id2-kd N2a cells and anti-CTLA4 antibody (FIG. 10A). Interestingly, all $CD8^+$ T cell depleted mice also developed tumors at the site of Id2-kd N2a cell vaccination (FIG. 10B), again demonstrating the importance of intact immunity. Mice lacking NK cells were for the most part able to reject their tumors following therapy (FIG. 10A). $CD4^+$ T cell depletion initially had minimal adverse effect on the therapeutic vaccine strategy and 75% of mice lacking $CD4^+$ T-cells remained tumor free for 4 weeks. Interestingly, all mice in the CD4 depletion group eventually developed delayed tumors, after the 4 week period (FIG. 10A). To determine if re-accumulation of $CD4^+$ regulatory T-cells (Treg) cells played a role in tumor relapse, cell infiltrates from the tumors of CD4 depleted mice were stained with anti-CD45, CD4 and FoxP3 antibodies. No evidence of Treg cell infiltrate (FIG. 10C) was identified; indicating that tumor relapse in $CD4^+$ T cell depleted mice is not mediated by the late accumulation of Treg cells. The most likely explanation is that depletion of $CD4^+$ T-cells during combined immunotherapy failed to help with activation of cytotoxic $CD8^+$ T-cells resulting in inadequate immunity. Inadequate immunity is shown by the need of CD4 help to obtain complete activation of CD8 cytotoxic T-cells. Taken together, these results showed that $CD4^+$ and $CD8^+$ T-cells were required for immunity and effective tumor cell elimination following combination immunotherapy.

Figure 11A:
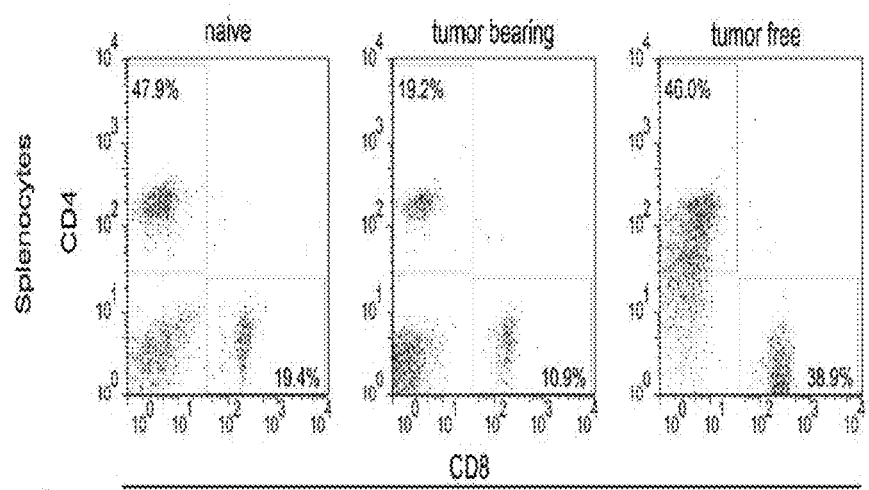
FIGS. 11A, 11B, 11C, 11D, 11E, 11F, and 11G show that an enhanced in vivo immune response mediates tumor clearance.
Figure 11B:
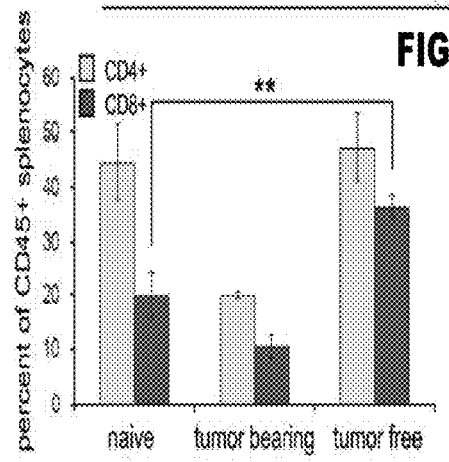
Figure 11C:
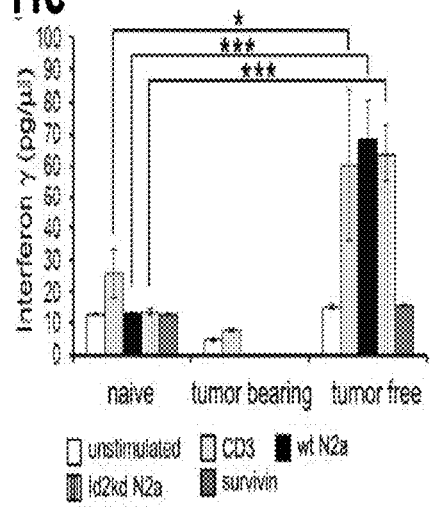

Robust T-Cell Immunity Mediated Tumor Rejection in Both Mouse and Human Neuroblastoma The prior studies provided evidence for T-cell immunity as a mechanism of tumor rejection following Id2-kd/checkpoint blockade therapy. The inventors thus sought to define the in vivo cellular response in mice that cleared tumor following combination therapy. Splenic $CD8^+$ T cell counts were significantly higher in mice that were vaccinated and cleared tumor, compared to naïve mice that were not vaccinated nor challenged with tumor (FIGS. 11A and 11B). The production of IFNγ from T-cells is a hallmark of immune cell response, thus we measured IFNγ secretion from splenocytes following antigen stimulation. The splenocytes of mice that cleared tumor secreted significant amounts of IFNγ following stimulation with wild type Neuro2a or Id2kd N2a cells (FIG. 11C) compared to splenocytes taken from naïve mice.

Figure 11D:
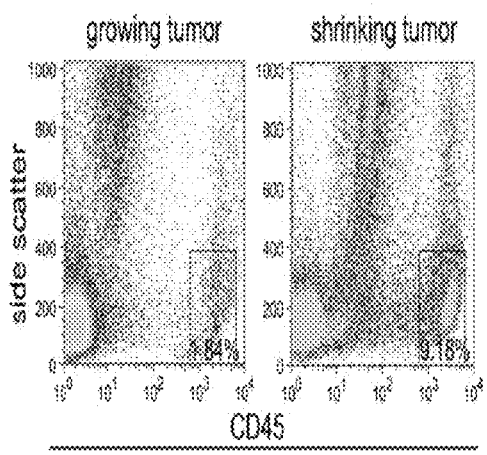
Figure 11E:
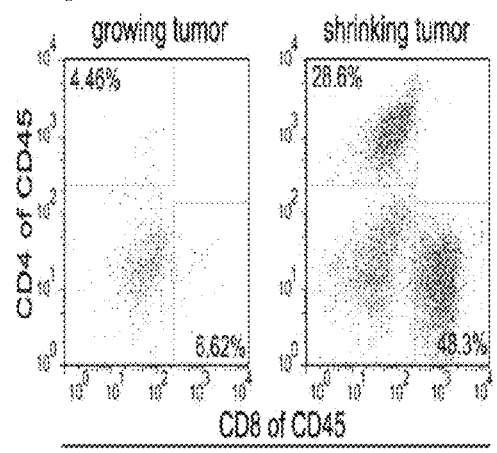
Figure 11F:
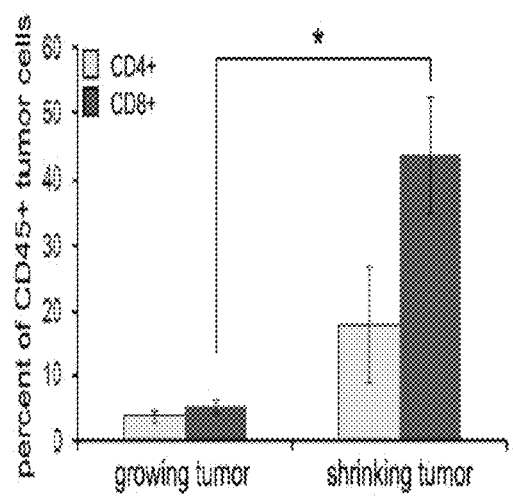
Figure 11G:
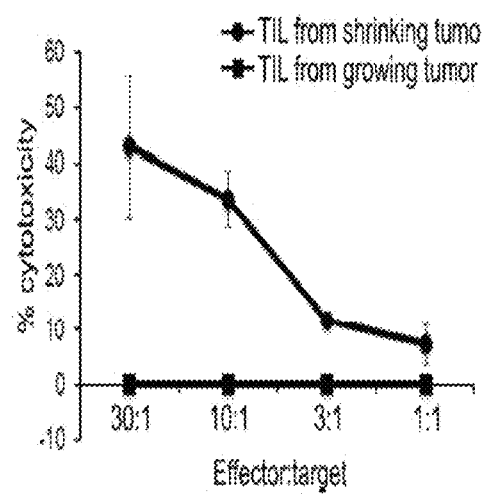

To gain more insight into the mechanism of tumor cell rejection, the microenvironment of shrinking mouse tumors by quantifying tumor infiltrating lymphocytes (TIL) following vaccination were investigated. TIL are frequently found in tumors and are effective at delaying tumor progression suggesting the potential influence of immune cell infiltrates on patient prognosis; Boon, et al., Immunol. Today 18:267-8 (1997); Galon, et al., Science 313:1960-4 (2006); Lee, et al., Cur. Oncol. Rep. 14:468-74 (2012); Zhang, et al., N. Engl. J. Med. 348:203-213 (2003). It was found that a massive increase in $CD45^+$ cells as well as a robust infiltration of $CD8^+$ T-cells in the shrinking tumors following combination immunotherapy (FIG. 11D-11F). To elucidate the effector function of the TIL, freshly isolated and purified tumor infiltrating $CD8^+$ T-cells were subjected to standard chromium-51 release assay. $CD8^+$ TIL exhibited potent cytotoxic activity against wild type Neuro2a cells without ex vivo recovery (FIG. 11G). This finding indicates the high functionality of these cells and further emphasizes the key role that $CD8^+$ T-cells play in inducing effective immunity and tumor regression.

Figure 12A:
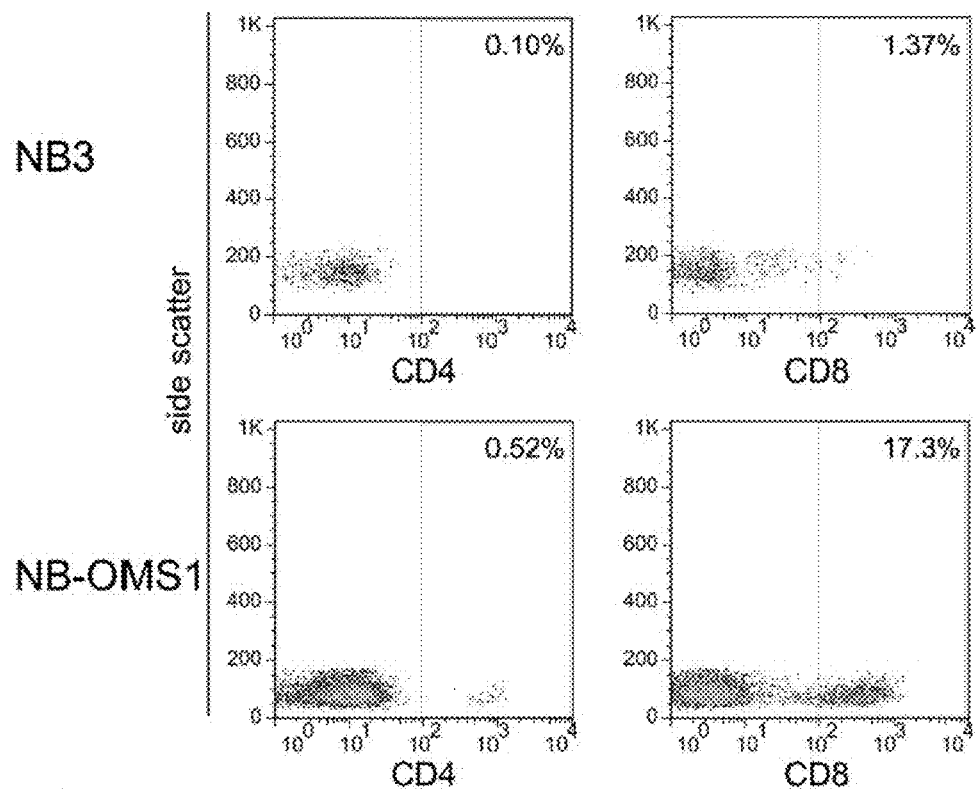
FIGS. 12A and 12B show presence of TIL in human neuroblastoma samples. Five freshly harvested human neuroblastoma specimens were analyzed for TIL; two of the tumors were from patients with Opsoclonus/myoclonus syndrome (OMS).
Figure 12B:
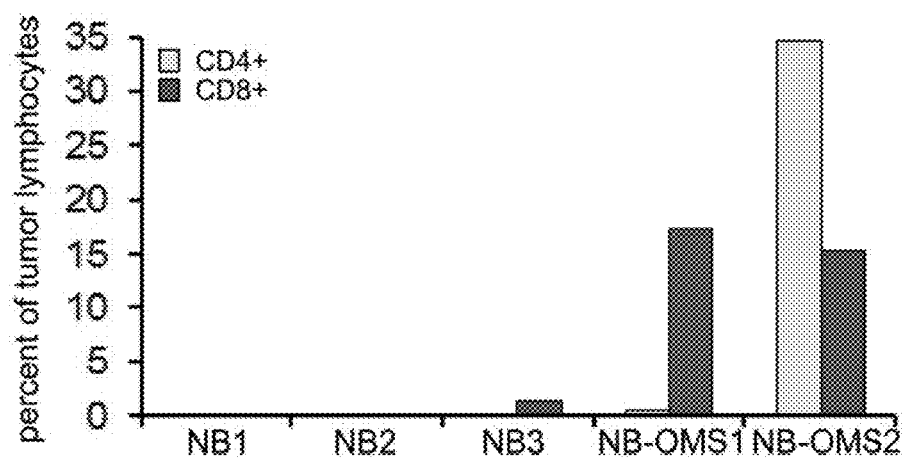

As a clinical correlate of T cell immunity in neuroblastoma the inventors examined freshly harvested human tumor specimens for TIL presence. It was observed that minimal $CD8^+$ cells in several tumors with poor prognosis (0 to 1.3% of tumor lymphocytes) (n=3), whereas in neuroblastoma tumors from patients with Opsoclonus Myoclonus Syndrome (OMS) (n=2) a robust infiltration of $CD8^+$ cells was noted (15.4 and 17.3% of tumor lymphocytes) (FIGS. 12A and 12B). It is now well documented that although childhood neuroblastoma carries a significant mortality rate, neuroblastomas associated with OMS tend to be low grade and have a significantly more favorable outcome; Altman, et al., Cancer 37: 846-852 (1976); Koh, et al., J. Pediatr. 125:712-716 (1994) Russo, et al., Med. Pediatr. Oncol. 28:284-288 (1997).

The ability of cancer cells to escape immune surveillance is a common hallmark of cancers with poor prognosis; Hanahan, et al., Cell 144: 646-674 (2011). Neuroblastoma is an example of a tumor with high-risk stratification, frequently exhibiting a poor prognosis and recurrent disease following initial therapy. Unlike several other childhood solid tumors, successful treatment of high-risk neuroblastoma remains a major challenge with limited effective therapeutic options. Strategies to circumvent treatment failures are intensively studied and amongst these strategies, immunotherapy has attracted much attention. The inventors' results offer a novel pre-clinical strategy combining targeted gene knock-down and checkpoint blockade as a potent, effective, tumor-specific vaccine strategy for neuroblastoma. This strategy is dependent on a robust cytotoxic CD8$^+$ T lymphocyte (CTL) response that is supported by CD4$^+$ T helper cells for tumor eradication.

Recent advances in the understanding of mechanisms regulating T-cell activation have made significant progress in cancer immunotherapy. The activation state of the innate immune system is thought to play a critical role in either the induction of immunity or tolerance after encountering tumor antigen.

In contrast to the considerable literature documenting immunological responses to melanoma in humans and in mouse models, there is a scarcity of data concerning immunological responses to neuroblastoma. Based on present concepts of immunogenicity, it comes as a surprise that live tumor cells induce an immune response at all. The whole tumor cell vaccine studied in this work, contains no pathogen associated molecular patterns nor artificial inflammatory cytokines; yet potent immunogenicity is attained by targeting a key molecule of reversible adaptive plasticity. Id2-kd N2a cells induced immunity in a syngeneic immune competent mouse model, yet these tumor cells grew unabated in immune-compromised hosts. In the immune competent host, long-term immunity was induced against subsequent wild-type tumor challenge and of clinical interest; immunogenicity of the knock-down cells was maintained following irradiation. The mechanism of tumor cell immunogenicity in Id2-kd cells is unknown, but is clearly a perturbation in molecular homeostasis of the tumor cells. Changes induced by targeting Id2 in the tumor cell could vary from increased antigenicity, enhanced antigen presenting cell uptake or loss of immune-suppressive or immune-evasive mechanisms. Four Id proteins (Id1, Id2, Id3 and Id4) are described; Lasorella, et al., Nat. Rev. Cancer 14:77-91 (2014)(incorporated by reference), and may function in a redundant manner.

The inventors specifically targeted Id2 in the mouse neuroblastoma cell line, as this was the most dominant and differentially expressed protein (~20 fold) between the anchorage dependent and independent cell phenotypes; Chakrabarti, et al., PLOS One e83521 (2012). In other mouse and human tumor cell lines Id2 was not dominant whereas Id1 and/or Id3 were. Id1 and/or Id3 may be better targets in other cancer types for inducing the attenuated, immunogenic effect observed following Id2 knock-down in Neuro2a cells. The effects described with Id2 targeting may be expanded to other cell lines.

Despite the presence of tumor associated antigens, tumor growth enhances antigen specific expansion of Treg inducing tumor tolerance; Nishikawa, et al., J. Exp. Med. 201: 681-686 (2005); Pardoll, et al Annu. Rev. Immunol. 21:807-839 (2003). Similarly, vaccination alone can induce limited immunity with expansion of regulatory T-cells or by inhibition of T-cell activation. Treatment with monoclonal antibody specific for cytotoxic T lymphocyte associated antigen-4 (CTLA-4), a checkpoint protein expressed on T-lymphocytes has emerged as an effective cancer therapy. The effect is most likely induced by both enhancing T-cell expansion and/or by selective Treg depletion within the tumor mass; Read, et al. J. Exp. Med. 192:295-302 (2000); Takahashi, et al., J. Exp. Med. 192:303-310 (2000). Immune checkpoint modulation has become a clinically relevant therapy approach in melanoma and lung cancer; Van Elsas, et al., J. Exp. Med. 190:355-366 (1999); Brahmer, et al., Cancer Immunol. Res. 1:85-91 (2013); Hamid, et al., N. Engl. J. Med. 369:134-144 (2013); in particular, anti-CTLA-4 antibody shows promising results in clinical trials in melanoma patients; Hodi, et al., N. Engl. J. Med. 363: 711-723 (2010); Robert, et al., N. Enl. J. Med. 364:2517-2526 (2011). Like melanoma, neuroblastoma is derived from neural crest stem cells and shares common antigenic determinants; Carrel, et al., Acta Neuropathol. 57: 158-164 (1982). The inventors' pre-clinical results provide a convincing treatment option, in which the combination of Id2kd neuroblastoma tumor cells and CTLA-4 antibody prime a functional tumor-specific T cell response, increase immune cell access to the tumor site, enhance anti-tumor immune cell function and eradicate significant tumor burden. The inventors' data in this primary tumor model indicates a synergy between CTLA-4 blockade and Id2-kd N2a cells. Mice treated with either the altered cells or antibody alone in the non-immunogenic aggressive tumor model had either marginal or no reduction in tumor growth, whereas the combination of both resulted in significant tumor clearance. This suggests that an additional source of antigen from the cell-based vaccine contributes to T cell priming, which is enhanced by blockade of CTLA-4 mediated inhibitory signals of T cell activation. The ideal timing of combination vaccination and checkpoint blockade administration is uncertain, but we observed improved cell rejection when anti-CTLA-4 antibody administration lagged several days behind Id2-kd N2a cell implantation. This finding suggests that a critical window exists in which antigen processing occurs prior to checkpoint blockade.

The inventors' results show that the vaccine's tumor ablative effect requires both CD8$^+$ and CD4$^+$ T cells. The immune cell depletion study proves that cytotoxic CD8$^+$ T-cells (CTL) are indispensable for tumor rejection, but also demonstrates the requirement for CD4$^+$ T cell help for effective induction of the CD8$^+$ CTL response. Furthermore, the inventors have demonstrated a massive influx of activated CD8$^+$ CTL in regressing mouse tumors as was also observed in two human neuroblastomas associated with Opsoclonus Myoclonus Syndrome (OMS). A large body of evidence has uncovered a correlation between the presence of lymphocyte infiltration and the survival of patients affected by many types of cancer including neuroblastoma; Galon, et al., Science 313:1960-1964 (2006), Zhang, et al., N. Engl. J. Med. 348:203-213 (2003); Carlson, et al., Oncoimmunol. 2:e23618 (2013); Deschoolmeester, et al., BMC Immunol. 11:19 (2010). In particular, presence of CD8$^+$ T-cells was associated with a favorable prognosis; Carlson, et al., Oncoimmunol. 2:e23618 (2013); Sato, et al., PNAS USA 102:18538-43 (2005); and is considered the major component of an effective immune response to most tumors. Evidence suggests children with coincident OMS and neuroblastoma have favorable outcome and become long term survivors; Altman, et al., Cancer 37: 846-852

(1976); Koh, et al., J. Pediatr. 125:712-716 (1994) Russo, et al., Med. Pediatr. Oncol. 28:284-288 (1997). Moreover, similar to our finding, diffuse and extensive lymphocytic infiltration was observed in neuroblastic tumors associated with OMS; Cooper, et al., Med. Pediatr. Oncol. 36:623-629, suggesting the role of immune surveillance in recognizing and eradicating unfavorable tumor cells in these patients.

The opsoclonus and myoclonus observed in this form of favorable OMS neuroblastoma is probably a secondary autoimmune response to tumor immunity. Despite the often rapid, potent and complete tumor rejection observed in our pre-clinical study, the mice remained well and showed no signs of illness in the form of potential autoimmunity. Although no specific testing was undertaken to evaluate immune related adverse events (irAEs) in the animals, they looked well and were followed for months following therapy. It is possible that the altered whole tumor cell vaccine preferentially targets tumor-specific antigens as opposed to tumor related antigens, but this postulation is speculative as the actual antigen targets are unknown. Although it is described that the threshold of inducing autoimmunity is lower than that of producing tumor immunity; Miska, et al., Eur. J. Immunol. 42:2584-96 (2012). While the well-being of the mice in this model is reassuring, further investigation prior to clinical translation is needed.

The work presented above demonstrates that an attenuated Id2-kd whole neuroblastoma cell vaccine is safe in mice; induces broad tumor-specific cellular immunity, protects against tumor formation in prophylactic tumor models and in combination with the clinically relevant checkpoint immune modulator CTLA-4 antibody, eradicates large established neuroblastoma tumors. This work should enable translation of our findings into a therapeutic patient-specific vaccine for resistant neuroblastoma tumors. The data also provide compelling evidence for the development of potent tumor specific vaccine strategies, based on the combination of targeted gene knock-down in tumor cells and checkpoint immune-modulation for other aggressive high-risk solid tumors.

Example 3

Effects of Combining Id-2 Knock-Down with Antibodies to CTLA-4 and PD-L1

We have recently shown that down regulation of Id2 in murine neuroblastoma cells (Id2-knock-down N2a ("Id-kd N2a") induced robust tumor cell immunity. Id2-knock-down whole tumor cells in combination with CTLA4 checkpoint blockade produced a potent, T-cell mediated vaccine capable of eradicating large established tumors. This vaccine strategy was paradoxically more effective in targeting a non-immunogenic tumor cell line (AgN2a, 90% cure) than it was in eradicating the immunogenic wild type tumor cell line (N2a, 60% cure). This study sought to determine 1.) whether a difference in PD-L1 expression between tumor cell phenotypes could explain this paradoxical inefficiency in curing mice with wild-type tumor and 2.) if targeting PD-L1 would enhance efficacy of the neuroblastoma vaccine strategy. Experimental procedures: The aggressive non-immunogenic subclone of N2a: AgN2a was produced by repeated in vivo passaging of tumor cells through immune competent mice. Gene array analysis as well as flow cytometry of cell surface staining was performed on N2a and AgN2a tumor cells to quantify differential expression of PD-L1 on tumor cells. Mice were challenged with WT N2a ($1\times10^6$) and once tumors were established, mice were then vaccinated with various combinations of Id2kd-N2a cells, and CTLA4/PD-L1 blocking antibodies. Results: Wild type N2a tumor cells expressed significantly higher levels of PD-L1 (ti.6 fold; p=0.0002) compared to the non-immunogenic AgN2a cell line. Id2-kd N2a and anti-CTLA-4 resulted in robust CD4 and CD8 T-cell responses, but cured only 60% of mice with established N2a tumors. Blocking PD-L1 alone or combining anti-PD-L1 with Id2-kd cells was ineffective against established neuroblastoma. When PD-L1 antibody was combined with the Id2-kd whole tumor cell vaccine plus CTLA-4 blockade, all mice were cured of established N2a tumors (n=10; 100% cure).

As shown by Examples 3A-3E below, Id2-kd enhanced tumor cell immunogenicity while CTLA-4 blockade primed and induced cytotoxic T-cell expansion. PD-L1 blockade enhanced tumor killing and most likely prevented T-cell exhaustion. The combination of Id2-kd whole cell vaccination with CTLA4 and PD-L1 blockade resulted in a curative immunotherapeutic strategy in a model of neuroblastoma.

Example 3A

As shown in FIG. 13A mouse Neuro2a neuroblastoma cells grown as AD and AI phenotypes. FIG. 13B shows the differential expression of Id2 in AD and AI phenotypes with higher expression of Id2 being found in the AD phenotype. Affymetrix array identified 1,180 differentially expressed genes in the AD and AI Neuro2a cells (Id2 expression was most notable: 20 fold higher in AD). As shown in FIG. 13C, Id2 is critical for driving reversible adaptive plasticity in which the AD phenotype (Id2$^+$) is proliferative, whereas the AI phenotype (Id2$^-$) is dormant. These phenotypes are promoted in vitro by presence of serum (AD) or EGF/FGF (AI). Tumors were shown to be heterogeneous and can contain cells with both the Id2$^+$ and Id2$^-$ phenotypes as shown in FIG. 13D.

Example 3B

Figure 14A:
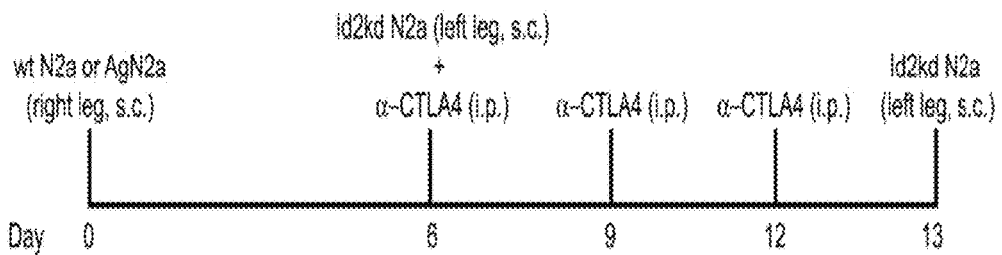
FIGS. 14A, 14B and 14C describe aspects of the therapeutic vaccine strategy.
Figure 14B:
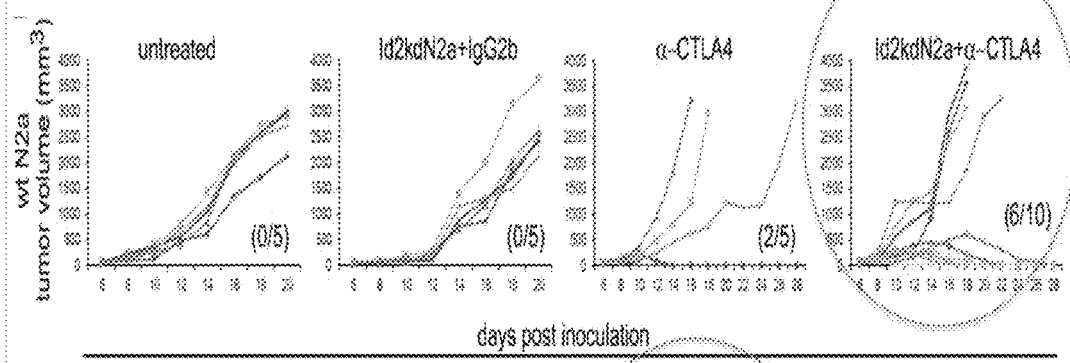
Figure 14C:
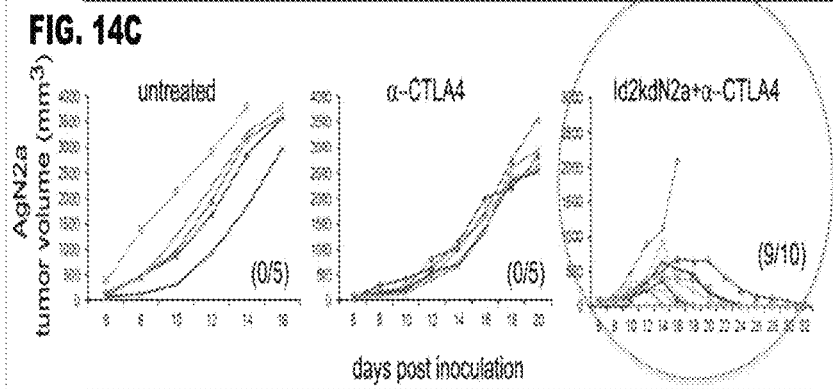

FIG. 14A shows a schematic diagram of the therapeutic vaccine strategy. Two established tumor models, namely Neuro2a (wtN2a) and AgN2a were tested, where mice challenged with either wtN2a or AgN2a cells were subjected to a combination immunotherapy with Id2kdN2a and α-CTLA4 antibody starting at day 6 after inoculation. Neuroblastoma tumors are normally visible (5 mm in diameter) in AJ mice by day 6. Tumor growth curves of wtN2a (FIG. 14B) and AgN2a (FIG. 14C) cells show that the Id2-kd tumor cell vaccination combined with immune-modulation cures mice with established tumor. The parenthesis indicates number of mice that survived tumor free.

Example 3C

As shown in FIG. 15A, representative flow cytometry plots showing CD4$^+$ and CD8$^+$ T-cells in CD45$^+$ splenocytes of naive (n=5), tumor bearing (n=3) and tumor free (n=5) mice. (15B) Graphical representation of (A) indicating significant (** $p=0.013$) increase in CD8$^+$ cells in the spleens of mice cleared of tumor. (15C) Splenocytes of mice that cleared tumor had enhanced IFNγ secretion following stimulation with CD3 (* $p<0.02$), wtN2a or Id2-kd-N2a cells (*** $p<0.0001$). (15D, 15E) Tumor infiltrating lymphocytes (TIL) following vaccination were quantified and a massive infiltration of CD8$^+$ T-cells was detected in the shrinking tumors (n=5) as opposed to the growing tumors (* $p<0.02$).

(15F) Chromium-51 release assay exhibited potent cytotoxic activity of CD8+ TIL from shrinking tumor (n=3); whereas the TIL isolated from growing tumors (n=4) show no activity at all. Data presented as mean+S.D.

Example 3D

Figure 16B:
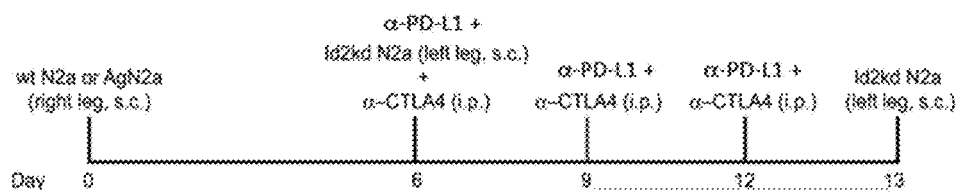
Figure 16C:
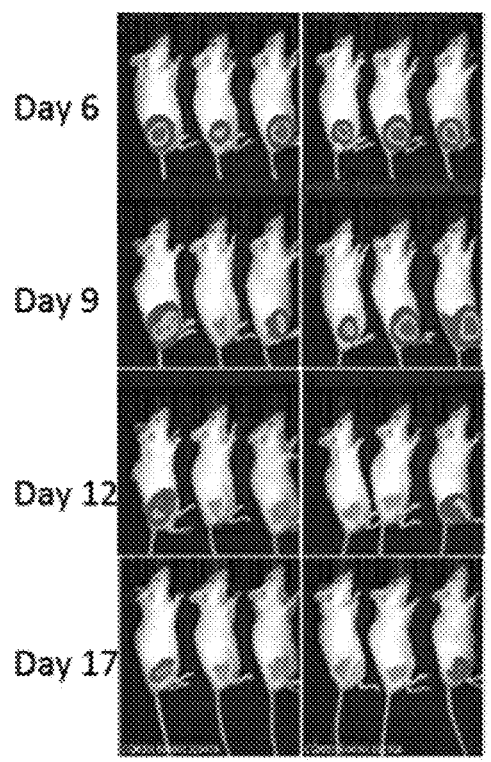

As shown in FIG. 16A gene array analysis and flow cytometry was performed on N2a and AgN2a tumor cells to quantify expression of PD-L1. A 3.7 fold increase in PD-L1 expression was noted in WT N2A by gene array and confirmed by flow cytometry. 16B. Mice were challenged with WT N2a (1×10$^6$) and once tumors were established, mice were vaccinated with various combinations of Id2-kd-N2a cells, and CTLA4/PD-L1 blocking antibodies. FIG. 16B depicts the vaccination protocol, while FIG. 16C shows tumor eradication in vaccinated mice as detected by chemiluminescent imaging.

Example 3E

Figure 17A:
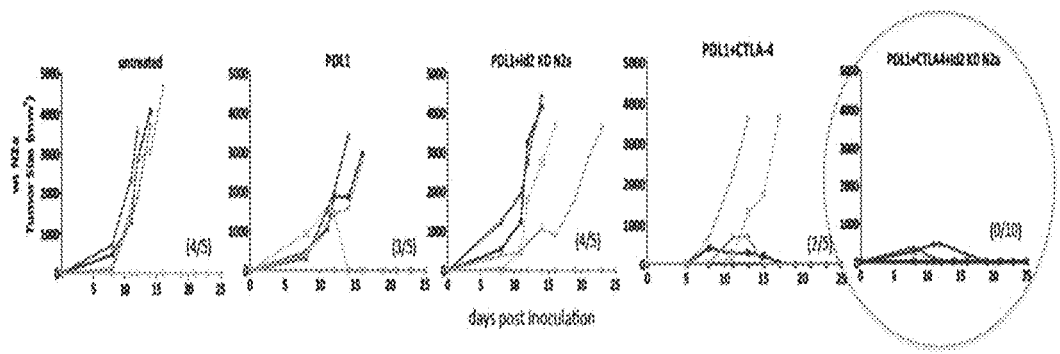
FIGS. 17A, 17B and 17C show the effect of vaccination on the treatment groups.
Figure 17B:
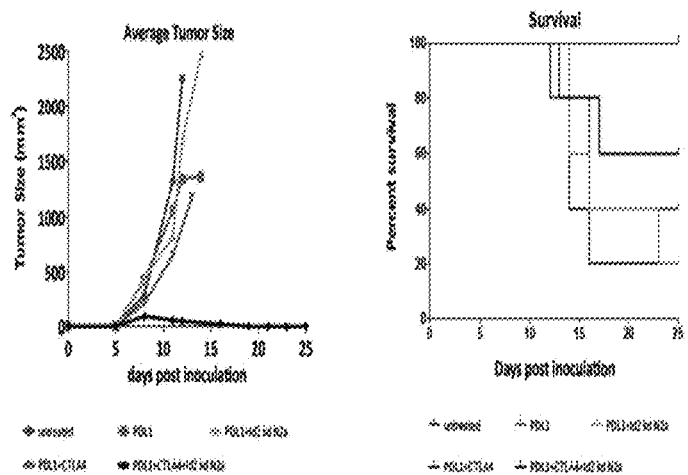
Figure 17C:
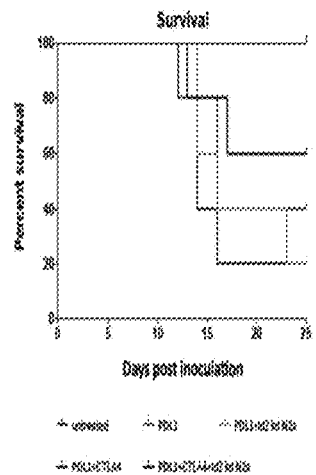
Figure 18:
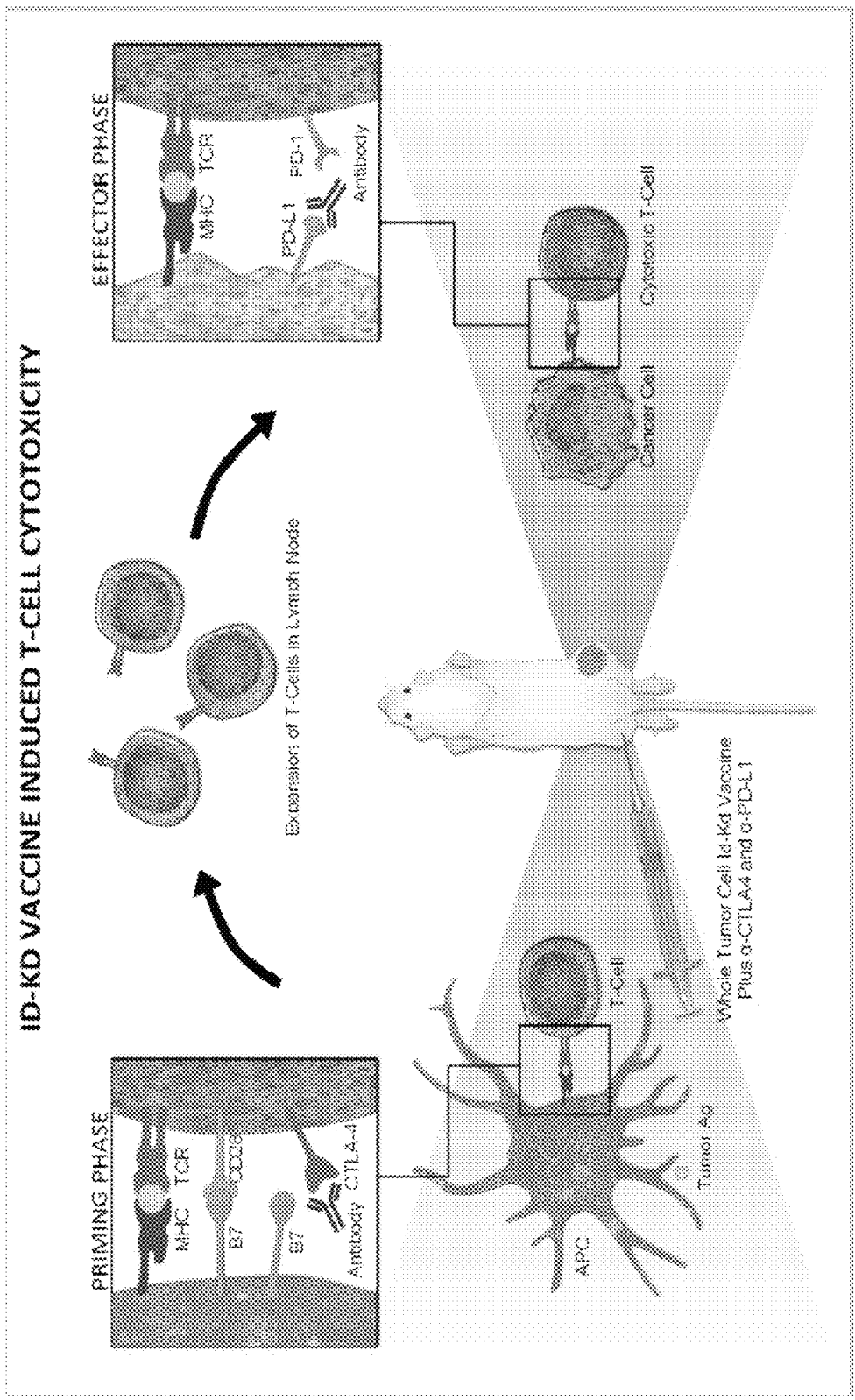
FIG. 18 illustrates one embodiment of the steps and interactions associated with induction of cytotoxic T-cells using an Id-knock-down vaccine.

As shown in FIG. 17A tumor growth in treatment groups following vaccination. 10 of 10 mice were cured when Id2-kd cells were combined with CTLA4 and PD-L1 checkpoint inhibition. (Number of mice with tumor: 0/10) FIGS. 15B and 15C depict average tumor size and survival in the various treatment groups.

The invention claimed is:

1. A method for treating neuroblastoma comprising immunizing a subject having neuroblastoma with autologous neuroblastoma cells modified to reduce an amount or activity of Id2 protein compared to an otherwise identical unmodified autologous cell.

2. The method of claim 1, wherein the autologous neuroblastoma cells express Id1 and/or Id3 and are further modified to reduce an amount or activity of Id1 protein, Id3 protein, or both Id1 and Id3 proteins.

3. The method of claim 1, wherein the Id2 protein comprises an amino acid sequence that is at least 95% identical to SEQ ID NO: 4 or 12.

4. A method for treating neuroblastoma comprising immunizing a subject having neuroblastoma with autologous neuroblastoma cells modified to reduce an amount or activity of Id1 protein compared to an otherwise identical unmodified autologous cell.

5. The method of claim 4, wherein the Id1 protein comprises an amino acid sequence that is at least 95% identical to SEQ ID NO: 2 or 10.

6. A method for treating neuroblastoma comprising immunizing a subject having neuroblastoma with autologous neuroblastoma cells modified to reduce an amount or activity of Id3 protein compared to an otherwise identical unmodified autologous cell.

7. The method of claim 6, wherein the Id3 protein comprises an amino acid sequence that is at least 95% identical to SEQ ID NO: 6 or 14.

* * * * *

SEQUENCE LISTING

<160> NUMBER OF SEQ ID NOS: 16

<210> SEQ ID NO 1
<211> LENGTH: 934
<212> TYPE: DNA
<213> ORGANISM: Mus musculus
<220> FEATURE:
<221> NAME/KEY: CDS
<222> LOCATION: (91)..(537)

<400> SEQUENCE: 1

```
tctcattgta caacctttct tcaacttctt gttctcttcc cacactctgt tctcagcctc      60
ctccgctccc ctccgcctgt tctcaggatc atg aag gtc gcc agt ggc agt gcc     114
                                 Met Lys Val Ala Ser Gly Ser Ala
                                  1               5 gca gcc gct gca ggc cct agc tgt tcg ctg aag gcg ggc agg aca gcg     162
Ala Ala Ala Ala Gly Pro Ser Cys Ser Leu Lys Ala Gly Arg Thr Ala
     10                  15                  20 ggc gag gtg gta ctt ggt ctg tcg gag caa agc gtg gcc atc tcg cgc     210
Gly Glu Val Val Leu Gly Leu Ser Glu Gln Ser Val Ala Ile Ser Arg
 25                  30                  35                  40 tgc gct ggg acg cgc ctg ccc gcc ttg ctg gac gag cag cag gtg aac     258
Cys Ala Gly Thr Arg Leu Pro Ala Leu Leu Asp Glu Gln Gln Val Asn
                 45                  50                  55 gtc ctg ctc tac gac atg aac ggc tgc tac tca cgc ctc aag gag ctg     306
Val Leu Leu Tyr Asp Met Asn Gly Cys Tyr Ser Arg Leu Lys Glu Leu
             60                  65                  70 gtg ccc acc ctg ccc cag aac cgc aaa gtg agc aag gtg gag atc ctg     354
Val Pro Thr Leu Pro Gln Asn Arg Lys Val Ser Lys Val Glu Ile Leu
         75                  80                  85 cag cat gta atc gac tac atc agg gac ctg cag ctg gag ctg aac tcg     402
Gln His Val Ile Asp Tyr Ile Arg Asp Leu Gln Leu Glu Leu Asn Ser
     90                  95                 100 gag tct gaa gtc ggg acc acc gga ggc cgg gga ctg cct gtc cgc gcc     450
Glu Ser Glu Val Gly Thr Thr Gly Gly Arg Gly Leu Pro Val Arg Ala
105                 110                 115                 120 ccg ctc agc acc ctg aac ggc gag atc agt gcc ttg gcg gcc gag gcg     498
Pro Leu Ser Thr Leu Asn Gly Glu Ile Ser Ala Leu Ala Ala Glu Ala
                125                 130                 135 gca tgt gtt cca gcc gac gat cgc atc ttg tgt cgc tga ggcggcgcac     547
Ala Cys Val Pro Ala Asp Asp Arg Ile Leu Cys Arg
            140                 145 tgagggacca gatggactcc agcccttcag gaggcaagag gaaaaaagtg ctctcggttc    607 cccagggat ctctgggaaa gacactaccg cagccaccgg actcttggcg gatcggtcca    667
gtgggtagag ggtttgatca acagagcctc accctctcca cctttcagcc tcagagact    727
```

```
ttggggaggg ggttaatcaa ccccgcgtgt ttctgttta  ttgaaaaagc agacatttt      787 ttttaaatgg tcacatttcg tgcttctcgg atttctgagg aaatattttg tattgtatat     847
tacaatgatc actggctgaa aatattgttt tacaatagtt ctatgggggt gagttttttg     907
ttgttattaa acaaacactt tagataa                                         934

<210> SEQ ID NO 2
<211> LENGTH: 148
<212> TYPE: PRT
<213> ORGANISM: Mus musculus

<400> SEQUENCE: 2

Met Lys Val Ala Ser Gly Ser Ala Ala Ala Ala Gly Pro Ser Cys
1               5                   10                  15

Ser Leu Lys Ala Gly Arg Thr Ala Gly Glu Val Val Leu Gly Leu Ser
                20                  25                  30

Glu Gln Ser Val Ala Ile Ser Arg Cys Ala Gly Thr Arg Leu Pro Ala
            35                  40                  45

Leu Leu Asp Glu Gln Gln Val Asn Val Leu Leu Tyr Asp Met Asn Gly
    50                  55                  60

Cys Tyr Ser Arg Leu Lys Glu Leu Val Pro Thr Leu Pro Gln Asn Arg
65                  70                  75                  80

Lys Val Ser Lys Val Glu Ile Leu Gln His Val Ile Asp Tyr Ile Arg
                85                  90                  95

Asp Leu Gln Leu Glu Leu Asn Ser Glu Ser Glu Val Gly Thr Thr Gly
            100                 105                 110

Gly Arg Gly Leu Pro Val Arg Ala Pro Leu Ser Thr Leu Asn Gly Glu
        115                 120                 125

Ile Ser Ala Leu Ala Ala Glu Ala Ala Cys Val Pro Ala Asp Asp Arg
    130                 135                 140

Ile Leu Cys Arg
145

<210> SEQ ID NO 3
<211> LENGTH: 1289
<212> TYPE: DNA
<213> ORGANISM: Mus musculus
<220> FEATURE:
<221> NAME/KEY: CDS
<222> LOCATION: (83)..(487)

<400> SEQUENCE: 3
tcattctgaa ccgagcctgg tgccgcgcag tcagctcagc ccctgtggc ggctccctcc       60 cggtcttcct cctacgagca gc atg aaa gcc ttc agt ccg gtg agg tcc gtt     112
                         Met Lys Ala Phe Ser Pro Val Arg Ser Val
                         1               5                   10 agg aaa aac agc ctg tcg gac cac agc ttg ggc atc tcc cgg agc aaa      160
Arg Lys Asn Ser Leu Ser Asp His Ser Leu Gly Ile Ser Arg Ser Lys
                15                  20                  25 acc ccg gtg gac gac ccg atg agt ctg ctc tac aac atg aac gac tgc      208
Thr Pro Val Asp Asp Pro Met Ser Leu Leu Tyr Asn Met Asn Asp Cys
            30                  35                  40 tac tcc aag ctc aag gaa ctg gtg ccc agc atc ccc cag aac aag aag      256
Tyr Ser Lys Leu Lys Glu Leu Val Pro Ser Ile Pro Gln Asn Lys Lys
        45                  50                  55 gtg acc aag atg gaa atc ctg cag cac gtc atc gat tac atc ttg gac      304
Val Thr Lys Met Glu Ile Leu Gln His Val Ile Asp Tyr Ile Leu Asp
    60                  65                  70
```

| | | |
|---|---|---|
| ctg cag atc gcc ctg gac tcg cat ccc act atc gtc agc ctg cat cac<br>Leu Gln Ile Ala Leu Asp Ser His Pro Thr Ile Val Ser Leu His His<br>75                     80                        85                      90 | | 352 |
| cag aga cct gga cag aac cag gcg tcc agg acg ccg ctg acc acc ctg<br>Gln Arg Pro Gly Gln Asn Gln Ala Ser Arg Thr Pro Leu Thr Thr Leu<br>                        95                                  100                        105 | | 400 |
| aac acg gac atc agc atc ctg tcc ttg cag gca tct gaa ttc cct tct<br>Asn Thr Asp Ile Ser Ile Leu Ser Leu Gln Ala Ser Glu Phe Pro Ser<br>                              110                              115                        120 | | 448 |
| gag ctt atg tcg aat gat agc aaa gta ctc tgt ggc taa ataaatggca<br>Glu Leu Met Ser Asn Asp Ser Lys Val Leu Cys Gly<br>             125                              130 | | 497 |
| tttggggact ttttttttc ttttactttt ctctttttct tttgcacaag aagaagtcta | | 557 |
| caagatcttt taagactttt gttatcagcc atttcaccag gagaacacgt tgaatggacc | | 617 |
| tttttaaaaa gaaagcggaa ggaaaactaa ggatgatcgt cttgcccagg tgtcgttctc | | 677 |
| cggcctggac tgtgataccg ttatttatga gagactttca gtgccctttc tacagttgga | | 737 |
| aggttttctt tatatactat tcccaccatg gggagcgaaa acgttaaaaa aaaaagaaaa | | 797 |
| aaatcacaag gaattgccca atgtaagcag actttgcctt ttcacaaagg tggagcgtga | | 857 |
| ataccagaag gacccagtat tcggttactt aaatgaagtc ttcggtcaga atggcctttt | | 917 |
| ttgacacgag cctactgaat gctgtgtata tatttatata taaatatata tatattgagt | | 977 |
| gaaccttgtg gactctttaa ttagagtttt cttgtatagt ggcagaaata acctatttct | | 1037 |
| gcattaaaat gtaatgacgt acttatgcta aacttttat aaaagtttag ttgtaaactt | | 1097 |
| aacccttta tacaaaataa atcaagtgtg tttattgaat gttgattgct tgctttattt | | 1157 |
| cagacaacca gtgctttgat ttttttatg ctatgttata actgaaccca aataaatacc | | 1217 |
| agttcaaatt tatgtagact gtattaagat tataataaaa tgtgtctgac atcaaaaaaa | | 1277 |
| aaaaaaaaaa aa | | 1289 |

<210> SEQ ID NO 4
<211> LENGTH: 134
<212> TYPE: PRT
<213> ORGANISM: Mus musculus

<400> SEQUENCE: 4

Met Lys Ala Phe Ser Pro Val Arg Ser Val Arg Lys Asn Ser Leu Ser
1                  5                         10                        15

Asp His Ser Leu Gly Ile Ser Arg Ser Lys Thr Pro Val Asp Asp Pro
                   20                        25                        30

Met Ser Leu Leu Tyr Asn Met Asn Asp Cys Tyr Ser Lys Leu Lys Glu
                   35                        40                        45

Leu Val Pro Ser Ile Pro Gln Asn Lys Lys Val Thr Lys Met Glu Ile
50                      55                        60

Leu Gln His Val Ile Asp Tyr Ile Leu Asp Leu Gln Ile Ala Leu Asp
65                     70                        75                        80

Ser His Pro Thr Ile Val Ser Leu His His Gln Arg Pro Gly Gln Asn
                   85                        90                        95

Gln Ala Ser Arg Thr Pro Leu Thr Thr Leu Asn Thr Asp Ile Ser Ile
                   100                      105                    110

Leu Ser Leu Gln Ala Ser Glu Phe Pro Ser Glu Leu Met Ser Asn Asp
               115                      120                    125

Ser Lys Val Leu Cys Gly
    130

<210> SEQ ID NO 5
<211> LENGTH: 964
<212> TYPE: DNA
<213> ORGANISM: Mus musculus
<220> FEATURE:
<221> NAME/KEY: CDS
<222> LOCATION: (58)..(417)

<400> SEQUENCE: 5

| | |
|---|---:|
| gcactgtttg ctgctttagg tgtctcttt cctccctctc tatctctact ctccaac | 57 |
| atg aag gcg ctg agc ccg gtg cgc ggc tgc tac gag gcg gtg tgc tgc<br>Met Lys Ala Leu Ser Pro Val Arg Gly Cys Tyr Glu Ala Val Cys Cys<br>1               5                    10                 15 | 105 |
| ctg tcg gaa cgt agc ctg gcc att gcg cga ggc cgt ggt aag agc ccg<br>Leu Ser Glu Arg Ser Leu Ala Ile Ala Arg Gly Arg Gly Lys Ser Pro<br>             20                   25                  30 | 153 |
| tcg acc gag gag cct ctt agc ctc ttg gac gac atg aac cac tgc tac<br>Ser Thr Glu Glu Pro Leu Ser Leu Leu Asp Asp Met Asn His Cys Tyr<br>               35                  40                 45 | 201 |
| tcg cgc ctg cgg gaa ctg gtg ccg gga gtc ccg cga ggc act cag ctt<br>Ser Arg Leu Arg Glu Leu Val Pro Gly Val Pro Arg Gly Thr Gln Leu<br>50                    55                    60 | 249 |
| agc cag gtg gaa atc ctg cag cgt gtc ata gac tac atc ctc gac ctt<br>Ser Gln Val Glu Ile Leu Gln Arg Val Ile Asp Tyr Ile Leu Asp Leu<br>65                    70                    75                 80 | 297 |
| cag gtg gtc ctg gca gag ccg gcg cct gga ccc ccg gac ggt ccg cat<br>Gln Val Val Leu Ala Glu Pro Ala Pro Gly Pro Pro Asp Gly Pro His<br>                      85                  90                 95 | 345 |
| ctc ccg atc cag aca gct gag ctc act ccg gaa ctt gtg atc tcc aag<br>Leu Pro Ile Gln Thr Ala Glu Leu Thr Pro Glu Leu Val Ile Ser Lys<br>             100                 105               110 | 393 |
| gac aag agg agc ttt tgc cac tga cccggtcgtc ctggcacctc ccgaacgcag<br>Asp Lys Arg Ser Phe Cys His<br>115 | 447 |
| gtgctggcgc ccgttccgct tgggaccctg ggactctggg accctctctc cagccggaag | 507 |
| cctgagggca tggatgagct tcgatcttaa cccagccctc ttcacttacc ctgaactcaa | 567 |
| cgcctcgagg ctgacctgg agcccgagag aaggactgaa cttgggtggc ctgaagagct | 627 |
| agcacacgct ggtcagcagc tgggcaacgt cactctgtcc ccaccctgac tcaagtctaa | 687 |
| aagactggct tttccgagaa tggggtgtcg agagggtgtg gggggatgcg agtggctgcc | 747 |
| ctgcgcactc tgccaaggca gcataagagc tgttcttctg gtttccttgg agaaaagctc | 807 |
| tgctgccctg attatgaact ctataataga gtatatagct tttgtacctt ttttacagga | 867 |
| aggtgacttt ctgtaatcat gtgatgtata ttaaactttt tataaaagtt aacattttgc | 927 |
| ataataaacc attttgaac actttgaaaa aaaaaaa | 964 |

<210> SEQ ID NO 6
<211> LENGTH: 119
<212> TYPE: PRT
<213> ORGANISM: Mus musculus

<400> SEQUENCE: 6

Met Lys Ala Leu Ser Pro Val Arg Gly Cys Tyr Glu Ala Val Cys Cys
1               5                    10                 15

Leu Ser Glu Arg Ser Leu Ala Ile Ala Arg Gly Arg Gly Lys Ser Pro
             20                   25                  30

Ser Thr Glu Glu Pro Leu Ser Leu Leu Asp Asp Met Asn His Cys Tyr
               35                  40                 45

```
Ser Arg Leu Arg Glu Leu Val Pro Gly Val Pro Arg Gly Thr Gln Leu
        50                  55                  60

Ser Gln Val Glu Ile Leu Gln Arg Val Ile Asp Tyr Ile Leu Asp Leu
 65                  70                  75                  80

Gln Val Val Leu Ala Glu Pro Ala Gly Pro Pro Asp Gly Pro His
                 85                  90                  95

Leu Pro Ile Gln Thr Ala Glu Leu Thr Pro Glu Leu Val Ile Ser Lys
                100                 105                 110

Asp Lys Arg Ser Phe Cys His
            115

<210> SEQ ID NO 7
<211> LENGTH: 1660
<212> TYPE: DNA
<213> ORGANISM: Mus musculus
<220> FEATURE:
<221> NAME/KEY: CDS
<222> LOCATION: (72)..(557)

<400> SEQUENCE: 7
agcaaattgc gggcggggac ccggagctcg ctctaccgct tgtcgcggtc ctctcgcgca      60
ggaagcgcgc g atg aag gcg gtg agc ccg gtg cgc ccc tcg ggc cgc aag     110
            Met Lys Ala Val Ser Pro Val Arg Pro Ser Gly Arg Lys
              1               5                  10 gcg ccg tcg ggc tgc ggc ggg gag ctg gcg cta cgc tgc ctg gcg           158
Ala Pro Ser Gly Cys Gly Gly Glu Leu Ala Leu Arg Cys Leu Ala
         15                  20                  25 gag cac ggc cac agc ctg ggt ggc tcg gca gcc gcc gcc gct gcg           206
Glu His Gly His Ser Leu Gly Gly Ser Ala Ala Ala Ala Ala Ala
 30                  35                  40                  45 gcg gcc gcg cgc tgc aag gcg gcc gag gcg gcg gcc gat gag ccg gcg       254
Ala Ala Ala Arg Cys Lys Ala Ala Glu Ala Ala Ala Asp Glu Pro Ala
                 50                  55                  60 ctg tgc ctg cag tgc gat atg aac gac tgc tac agt cgc ctg cgg agg       302
Leu Cys Leu Gln Cys Asp Met Asn Asp Cys Tyr Ser Arg Leu Arg Arg
             65                  70                  75 ctc gtg cct acc atc ccg ccc aac aag aaa gtc agc aaa gtg gag atc       350
Leu Val Pro Thr Ile Pro Pro Asn Lys Lys Val Ser Lys Val Glu Ile
 80                  85                  90 ctg cag cac gtt atc gac tac atc ctg gac ctg cag ctg gcg ctg gag       398
Leu Gln His Val Ile Asp Tyr Ile Leu Asp Leu Gln Leu Ala Leu Glu
     95                 100                 105 act cac cct gct ttg ctg aga cag ccg cca ccg ccc gcg cca cct ctc       446
Thr His Pro Ala Leu Leu Arg Gln Pro Pro Pro Pro Ala Pro Pro Leu
110                 115                 120                 125 cac ccg gcc ggg gct tgt ccg gtc gcg ccg ccg cgg acc cca ctc acc       494
His Pro Ala Gly Ala Cys Pro Val Ala Pro Pro Arg Thr Pro Leu Thr
                130                 135                 140 gcg ctc aac act gac ccg gcc ggc gcc gtg aac aag cag ggt gac agc       542
Ala Leu Asn Thr Asp Pro Ala Gly Ala Val Asn Lys Gln Gly Asp Ser
                145                 150                 155 att ctc tgc cgc tga gctgcgatgg atggccaggt gtgcggccgc ctgagcacca      597
Ile Leu Cys Arg
        160 gcgagccagg agccctagga agggagggcc agagcagaaa ttaagagaaa caagccaccg    657 gaggaaaggg gggaaatct tcagcaaatc tagaaacgtc gtctcgtctt gtcattccaa     717 gagagagaga gagagagaga gagaagggga aaaataaaac ttaaattcac ttttactttt    777
```

```
tttgcacgtt cacgagcatt caccgtacgt attctctttc gtttcttctt ttatgaccgc    837
tgtgaattgt acgtttctgt ggttattttt atcacccttt tgaaggtgca gttaaacttc    897
gaagcttaag tgttgtcgac cagactgcta agtagaagag caatcgtgaa tccaaccttta   957 gaggctacat tgtgacaagg gaactgtttt tgttttttgaa gctttactaa tataccagag  1017
cactgtagat atgttgtttt acatctattg tttaaaatag atgattataa cagggcgggg  1077 aacttttttct ctgcaagaat gttacatatt gtatagataa gtgagtgaca tttcatacccc 1137 tgtatatata gagatgttct ataagtgtga gaaagtatat gcgctttaat agactactgt  1197
aattataaga tattttttaat taaatatttt ttgtaaatat tatgtgtctg tttttttaaa  1257
atcgatggga atatttcttt tggaaaatta ttttttcagct cccttgcaga gcttttgcta  1317
tctggatgtt ttctgtttgg ccaggctgtt gatttggttt ttttgttttg ttttgcccag  1377
tatccagttt ctgaggctca gaggtaacag ctctctggta ctggtcttgc atgattgcat  1437
gaggtgttca atcacaaaat aaaccagtta cgagtccttt caaatgtgct ttctttaacc  1497
tagatggaaa cctttgtatt tgacgtgtac atggtaaaaa cctaccttct cgggttttaa  1557
gtacagggtt ttatagtgta atatataaag aattaagtgt gtggggtttt tattattatt  1617 attcttttttg aactgaggtc aaaaatagat tctgagtgaa ttc                    1660

<210> SEQ ID NO 8
<211> LENGTH: 161
<212> TYPE: PRT
<213> ORGANISM: Mus musculus

<400> SEQUENCE: 8

Met Lys Ala Val Ser Pro Val Arg Pro Ser Gly Arg Lys Ala Pro Ser
1               5                   10                  15

Gly Cys Gly Gly Gly Glu Leu Ala Leu Arg Cys Leu Ala Glu His Gly
            20                  25                  30

His Ser Leu Gly Gly Ser Ala Ala Ala Ala Ala Ala Ala Ala Ala Ala
        35                  40                  45

Arg Cys Lys Ala Ala Glu Ala Ala Asp Glu Pro Ala Leu Cys Leu
    50                  55                  60

Gln Cys Asp Met Asn Asp Cys Tyr Ser Arg Leu Arg Arg Leu Val Pro
65                  70                  75                  80

Thr Ile Pro Pro Asn Lys Lys Val Ser Lys Val Glu Ile Leu Gln His
                85                  90                  95

Val Ile Asp Tyr Ile Leu Asp Leu Gln Leu Ala Leu Glu Thr His Pro
            100                 105                 110

Ala Leu Leu Arg Gln Pro Pro Pro Ala Pro Pro Leu His Pro Ala
        115                 120                 125

Gly Ala Cys Pro Val Ala Pro Pro Arg Thr Pro Leu Thr Ala Leu Asn
    130                 135                 140

Thr Asp Pro Ala Gly Ala Val Asn Lys Gln Gly Asp Ser Ile Leu Cys
145                 150                 155                 160

Arg

<210> SEQ ID NO 9
<211> LENGTH: 926
<212> TYPE: DNA
<213> ORGANISM: Homo sapiens
<220> FEATURE:
<221> NAME/KEY: CDS
<222> LOCATION: (36)..(500)
```

<400> SEQUENCE: 9

```
ggggcccatt ctgtttcagc cagtcgccaa gaatc atg aaa gtc gcc agt ggc        53
                                      Met Lys Val Ala Ser Gly
                                      1               5 agc acc gcc acc gcc gcc gcg ggc ccc agc tgc gcg ctg aag gcc ggc       101
Ser Thr Ala Thr Ala Ala Ala Gly Pro Ser Cys Ala Leu Lys Ala Gly
            10                  15                  20 aag aca gcg agc ggt gcg ggc gag gtg gtg cgc tgt ctg tct gag cag       149
Lys Thr Ala Ser Gly Ala Gly Glu Val Val Arg Cys Leu Ser Glu Gln
                25                  30                  35 agc gtg gcc atc tcg cgc tgc cgg ggc gcc ggg gcg cgc ctg cct gcc       197
Ser Val Ala Ile Ser Arg Cys Arg Gly Ala Gly Ala Arg Leu Pro Ala
        40                  45                  50 ctg ctg gac gag cag cag gta aac gtg ctg ctc tac gac atg aac ggc       245
Leu Leu Asp Glu Gln Gln Val Asn Val Leu Leu Tyr Asp Met Asn Gly
55                  60                  65                  70 tgt tac tca cgc ctc aag gag ctg gtg ccc acc ctg ccc cag aac cgc       293
Cys Tyr Ser Arg Leu Lys Glu Leu Val Pro Thr Leu Pro Gln Asn Arg
                75                  80                  85 aag gtg agc aag gtg gag att ctc cag cac gtc atc gac tac atc agg       341
Lys Val Ser Lys Val Glu Ile Leu Gln His Val Ile Asp Tyr Ile Arg
            90                  95                 100 gac ctt cag ttg gag ctg aac tcg gaa tcc gaa gtt ggg acc ccc ggg       389
Asp Leu Gln Leu Glu Leu Asn Ser Glu Ser Glu Val Gly Thr Pro Gly
        105                 110                 115 ggc cga ggg ctg ccg gtc cgg gct ccg ctc agc acc ctc aac ggc gag       437
Gly Arg Gly Leu Pro Val Arg Ala Pro Leu Ser Thr Leu Asn Gly Glu
    120                 125                 130 atc agc gcc ctg acg gcc gag gcg gca tgc gtt cct gcg gac gat cgc       485
Ile Ser Ala Leu Thr Ala Glu Ala Ala Cys Val Pro Ala Asp Asp Arg
135                 140                 145                 150 atc ttg tgt cgc tga agcgcctccc ccagggaccg gcggacccca gccatccagg       540
Ile Leu Cys Arg gggcaagagg aattacgtgc tctgtgggtc tcccccaacg cgcctcgccg gatctgaggg     600
agaacaagac cgatcggcgg ccactgcgcc cttaactgca tccagcctgg ggctgaggct     660
gaggcactgg cgaggagagg cgctcctct ctgcacacct actagtcacc agagacttta     720
gggggtggga ttccactcgt gtgtttctat tttttgaaaa gcagacattt taaaaaatgg     780
tcacgtttgg tgcttctcag atttctgagg aaattgcttt gtattgtata ttacaatgat     840
caccgactga gaatattgtt ttacaatagt tctgtggggc tgttttttg ttattaaaca      900 aataatttag atggtgaaaa aaaaaa                                          926
```

<210> SEQ ID NO 10
<211> LENGTH: 154
<212> TYPE: PRT
<213> ORGANISM: Homo sapiens

<400> SEQUENCE: 10

```
Met Lys Val Ala Ser Gly Ser Thr Ala Thr Ala Ala Ala Gly Pro Ser
1               5                   10                  15

Cys Ala Leu Lys Ala Gly Lys Thr Ala Ser Gly Ala Gly Glu Val Val
            20                  25                  30

Arg Cys Leu Ser Glu Gln Ser Val Ala Ile Ser Arg Cys Arg Gly Ala
        35                  40                  45

Gly Ala Arg Leu Pro Ala Leu Leu Asp Glu Gln Gln Val Asn Val Leu
    50                  55                  60
```

```
Leu Tyr Asp Met Asn Gly Cys Tyr Ser Arg Leu Lys Glu Leu Val Pro
 65                  70                  75                  80

Thr Leu Pro Gln Asn Arg Lys Val Ser Lys Val Glu Ile Leu Gln His
                 85                  90                  95

Val Ile Asp Tyr Ile Arg Asp Leu Gln Leu Glu Leu Asn Ser Glu Ser
            100                 105                 110

Glu Val Gly Thr Pro Gly Gly Arg Gly Leu Pro Val Arg Ala Pro Leu
        115                 120                 125

Ser Thr Leu Asn Gly Glu Ile Ser Ala Leu Thr Glu Ala Ala Cys
130                 135                 140

Val Pro Ala Asp Asp Arg Ile Leu Cys Arg
145                 150

<210> SEQ ID NO 11
<211> LENGTH: 1402
<212> TYPE: DNA
<213> ORGANISM: Homo sapiens
<220> FEATURE:
<221> NAME/KEY: CDS
<222> LOCATION: (184)..(588)

<400> SEQUENCE: 11
ggggacgaag gaagctcca gcgtgtggcc ccggcgagtg cggataaaag ccgccccgcc      60 gggctcggc ttcattctga gccgagcccg gtgccaagcg cagctagctc agcaggcggc     120
agcggcggcc tgagcttcag ggcagccagc tccctcccgg tctcgccttc cctcgcggtc    180 agc atg aaa gcc ttc agt ccc gtg agg tcc gtt agg aaa aac agc ctg      228
    Met Lys Ala Phe Ser Pro Val Arg Ser Val Arg Lys Asn Ser Leu
     1               5                  10                  15 tcg gac cac agc ctg ggc atc tcc cgg agc aaa acc cct gtg gac gac      276
Ser Asp His Ser Leu Gly Ile Ser Arg Ser Lys Thr Pro Val Asp Asp
                 20                  25                  30 ccg atg agc ctg cta tac aac atg aac gac tgc tac tcc aag ctc aag      324
Pro Met Ser Leu Leu Tyr Asn Met Asn Asp Cys Tyr Ser Lys Leu Lys
             35                  40                  45 gag ctg gtg ccc agc atc ccc cag aac aag aag gtg agc aag atg gaa      372
Glu Leu Val Pro Ser Ile Pro Gln Asn Lys Lys Val Ser Lys Met Glu
         50                  55                  60 atc ctg cag cac gtc atc gac tac atc ttg gac ctg cag atc gcc ctg      420
Ile Leu Gln His Val Ile Asp Tyr Ile Leu Asp Leu Gln Ile Ala Leu
 65                  70                  75 gac tcg cat ccc act att gtc agc ctg cat cac cag aga ccc ggg cag      468
Asp Ser His Pro Thr Ile Val Ser Leu His His Gln Arg Pro Gly Gln
 80                  85                  90                  95 aac cag gcg tcc agg acg ccg ctg acc acc ctc aac acg gat atc agc      516
Asn Gln Ala Ser Arg Thr Pro Leu Thr Thr Leu Asn Thr Asp Ile Ser
                100                 105                 110 atc ctg tcc ttg cag gct tct gaa ttc cct tct gag tta atg tca aat      564
Ile Leu Ser Leu Gln Ala Ser Glu Phe Pro Ser Glu Leu Met Ser Asn
            115                 120                 125 gac agc aaa gca ctg tgt ggc tga ataagcggtg ttcatgattt cttttattct     618
Asp Ser Lys Ala Leu Cys Gly
            130 ttgcacaaca acaacaacaa caaattcacg gaatctttta agtgctgaac ttattttca     678 accatttcac aaggaggaca agttgaatgg acctttttaa aaagaaaaaa aaaatggaag    738 gaaaactaag aatgatcatc ttcccagggt gttctcttac ttggactgtg atattcgtta   798 tttatgaaaa agacttttaa atgcccttc tgcagttgga aggttttctt tatatactat    858
```

```
tcccaccatg gggagcgaaa acgttaaaat cacaaggaat tgcccaatct aagcagactt    918
tgcctttttt caaaggtgga gcgtgaatac cagaaggatc cagtattcag tcacttaaat    978
gaagtctttt ggtcagaaat tacctttttg acacaagcct actgaatgct gtgtatatat   1038
ttatatataa atatatctat ttgagtgaaa ccttgtgaac tctttaatta gagttttctt   1098
gtatagtggc agagatgtct atttctgcat tcaaaagtgt aatgatgtac ttattcatgc   1158 taaactttt ataaaagttt agttgtaaac ttaacccttt tatacaaaat aaatcaagtg    1218
tgtttattga atggtgattg cctgctttat ttcagaggac cagtgctttg attttatta    1278 tgctatgtta taactgaacc caaataaata caagttcaaa tttatgtaga ctgtataaga   1338
ttataataaa acatgtctga agtcaaaaaa aaaaaaaaaa aaaaaaaaaa aaaaaaaaaa   1398
aaaa                                                                1402
```

<210> SEQ ID NO 12
<211> LENGTH: 134
<212> TYPE: PRT
<213> ORGANISM: Homo sapiens

<400> SEQUENCE: 12

```
Met Lys Ala Phe Ser Pro Val Arg Ser Val Arg Lys Asn Ser Leu Ser
1               5                   10                  15

Asp His Ser Leu Gly Ile Ser Arg Ser Lys Thr Pro Val Asp Asp Pro
            20                  25                  30

Met Ser Leu Leu Tyr Asn Met Asn Asp Cys Tyr Ser Lys Leu Lys Glu
        35                  40                  45

Leu Val Pro Ser Ile Pro Gln Asn Lys Lys Val Ser Lys Met Glu Ile
    50                  55                  60

Leu Gln His Val Ile Asp Tyr Ile Leu Asp Leu Gln Ile Ala Leu Asp
65                  70                  75                  80

Ser His Pro Thr Ile Val Ser Leu His His Gln Arg Pro Gly Gln Asn
                85                  90                  95

Gln Ala Ser Arg Thr Pro Leu Thr Thr Leu Asn Thr Asp Ile Ser Ile
            100                 105                 110

Leu Ser Leu Gln Ala Ser Glu Phe Pro Ser Glu Leu Met Ser Asn Asp
        115                 120                 125

Ser Lys Ala Leu Cys Gly
    130
```

<210> SEQ ID NO 13
<211> LENGTH: 2481
<212> TYPE: DNA
<213> ORGANISM: Homo sapiens

<400> SEQUENCE: 13

```
agctttcttc ttttccctgt tgctcaaata aatagtgttc tttgctcaaa ccccctttcc     60
ctcctccttc tgcaatctca gcgcctagcg aaatctgttt tcttcattgt aacctcagct    120
tcaccgcaat taattttttt tccctctggt cacaagataa ttcctgacgc cagtgagtct    180
ggaggtcaga cgaacagcaa attggggaac aaggcggcac taattcctta caagttcctt    240
gaaaaatctt tcgcttaaaa aaaacggggg gtgggggag cttctttgct gttcaggat     300 ttatgcctcg cggagctgtg gctcgaacca gtgttggcta aggcggactg cagggggcag    360
ggaagctcaa agatctgggg tgctgccagg aaaaagcaaa ttctggaagt taatggtttt    420
gagtgatttt taaatccttg ctggcggaga ggcccgcctc tccccggtat cagcgcttcc    480
```

```
tcattctttg aatccgcggc tccgcggtct tcggcgtcag accagccgga ggaagcctgt    540
ttgcaattta agcgggctgt gaacgcccag ggccggcggg ggcagggccg aggcgggcca    600
ttttgaataa agaggcgtgc cttccaggca ggctctataa gtgaccgccg cggcgagcgt    660
gcgcgcgttg caggtcactg tagcggactt cttttggttt tctttctctt tggggcacct    720
ctggactcac tccccagcat gaaggcgctg agccggtgc gcggctgcta cgaggcggtg     780
tgctgcctgt cggaacgcag tctgccatc gcccggggcc gagggaaggg cccggcagct     840
gaggagccgc tgagcttgct ggacgacatg aaccactgct actcccgcct gcgggaactg    900
gtacccggag tcccgagagg cactcagctt agccaggtgg aaatcctaca gcgcgtcatc    960
gactacattc tcgacctgca ggtagtcctg gccgagccag cccctggacc ccctgatggc   1020
ccccaccttc ccatccaggt aagcctcgaa gtcgggacag gctgaacac ccaggcaagg    1080
atgctgcggg accctcggag ctcccgattg cctcgcgtaa ctcttccctc ttttcctcta   1140
atcagacagc cgagctcgct ccggaacttg tcatctccaa cgacaaaagg agcttttgcc   1200
actgactcgg ccgtgtcctg cacctccag gtgagtatct cctctcttgg agagggaggt    1260
ttaaacggca agtcctggag ttggcagacg ttttgaaaaa ttgccactca ctcggtttag   1320
ggaaactgag gccagagagg gacaagtgac ttgcccatgg ttgcatcaaa tgaatggcag   1380
agtcagtttc catgtgatgt gcatttaagc cttaatgcgc ctggccctgc ctccgcagtg   1440
gccgaggtct ggcaagtaga catggtccga ctaaatacaa gtctttctgt tccatgttgt   1500
ataggagctg tcttcggcag ccccctccca gctagtgtca attccaagta ggaggggtag   1560
cgcaacgtcc gcctgtggtc tttggcgcca actgggtggg ggcagcgtgg ggggcggagt   1620
tatcaggctg gaggtacaga ccaagtttcc tccctggcgc cggccagtct gcggacggcc   1680
cccgcctcgg cacgctcggc ggaaactgac tgctccttgg tcttctttcc tcccccgccc   1740
agaacgcagg tgctggcgcc cgttctgcct gggaccccgg gaacctctcc tgccggaagc   1800
cggacggcag ggatgggccc caacttcgcc ctgcccactt gacttcacca aatcccttcc   1860
tggagactaa acctggtgct caggagcgaa ggactgtgaa cttgtggcct gaagagccag   1920
agctagctct ggccaccagc tgggcgacgt caccctgctc ccaccccacc cccaagttct   1980
aaggtctttt cagagcgtgg aggtgtggaa ggagtggctg ctctccaaac tatgccaagg   2040
cggcggcaga gctggtcttc tggtctcctt ggagaaaggt tctgttgccc tgatttatga   2100
actctataat agagtatata ggttttgtac cttttttaca ggaaggtgac tttctgtaac   2160
aatgcgatgt atattaaact tttataaaa gttaacattt tgcataataa acgattttta   2220
aacacttgtg tatatgatga cacccgtctc cattaagtac taatgatgct ttctcgcaca   2280
tggccgaatt ttgggagctt tgggaaagtg aacttgctta ttctacgaga gggaaatgaa   2340
aaactgcctg gttgagaggg gatggggtgg agagagaagg gttcatgatg ggagtctcat   2400
gtccattgag ggatgggtgc agagaaaagt tctggctctg cctcattatt tcagagatga   2460
aaccagagac tggtgcaagc t                                              2481
```

<210> SEQ ID NO 14
<211> LENGTH: 119
<212> TYPE: PRT
<213> ORGANISM: Homo sapiens

<400> SEQUENCE: 14

Met Lys Ala Leu Ser Pro Val Arg Gly Cys Tyr Glu Ala Val Cys Cys
1               5                   10                  15

```
Leu Ser Glu Arg Ser Leu Ala Ile Ala Arg Gly Arg Gly Lys Gly Pro
             20                  25                  30
Ala Ala Glu Glu Pro Leu Ser Leu Leu Asp Asp Met Asn His Cys Tyr
         35                  40                  45
Ser Arg Leu Arg Glu Leu Val Pro Gly Val Pro Arg Gly Thr Gln Leu
     50                  55                  60
Ser Gln Val Glu Ile Leu Gln Arg Val Ile Asp Tyr Ile Leu Asp Leu
 65                  70                  75                  80
Gln Val Val Leu Ala Glu Pro Ala Gly Pro Pro Asp Gly Pro His
                 85                  90                  95
Leu Pro Ile Gln Thr Ala Glu Leu Ala Pro Glu Leu Val Ile Ser Asn
            100                 105                 110
Asp Lys Arg Ser Phe Cys His
            115

<210> SEQ ID NO 15
<211> LENGTH: 3891
<212> TYPE: DNA
<213> ORGANISM: Homo sapiens
<220> FEATURE:
<221> NAME/KEY: CDS
<222> LOCATION: (386)..(871)

<400> SEQUENCE: 15
gagagcgtag tggaggaggc gcggttgtga gtagtaccgg gagtggggtg atcccgggct    60
aggggagcgc ggcggccgcg atcgggctta gtcgagctc cgaagggagt gactaggaca    120
cccgggtggg ctactttcct tccggtgctt ttgcttttt tttccttgg gctcgggctg     180 agtgtcgccc actgagcaaa gattccctcg taaaacccag agcgaccctc ccgtcaattg    240
ttgggctcgg gagtgtcgcg gtgccccgag cgcgccgggc gcgaggcaa agggagcgga    300 gccggccgcg gacggggccc ggagcttgcc tgcctccctc gctcgcccca gcgggttcgc    360
tcgcgtagag cgcagggcgc gcgcg atg aag gcg gtg agc ccg gtg cgc ccc    412
                             Met Lys Ala Val Ser Pro Val Arg Pro
                               1               5 tcg ggc cgc aag gcg ccg tcg ggc tgc ggc ggc ggg gag ctg gcg ctg    460
Ser Gly Arg Lys Ala Pro Ser Gly Cys Gly Gly Gly Glu Leu Ala Leu
 10                  15                  20                  25 cgc tgc ctg gcc gag cac ggc cac agc ctg ggt ggc tcc gca gcc gcg    508
Arg Cys Leu Ala Glu His Gly His Ser Leu Gly Gly Ser Ala Ala Ala
                 30                  35                  40 gcg gcg gcg gcg gcg gca gcg cgc tgt aag gcg gcc gag gcg gcg gcc    556
Ala Ala Ala Ala Ala Ala Arg Cys Lys Ala Ala Glu Ala Ala Ala
             45                  50                  55 gac gag ccg gcg ctg tgc ctg cag tgc gat atg aac gac tgc tat agc    604
Asp Glu Pro Ala Leu Cys Leu Gln Cys Asp Met Asn Asp Cys Tyr Ser
         60                  65                  70 cgc ctg cgg agg ctg gtg ccc acc atc ccg ccc aac aag aaa gtc agc    652
Arg Leu Arg Arg Leu Val Pro Thr Ile Pro Pro Asn Lys Lys Val Ser
     75                  80                  85 aaa gtg gag atc ctg cag cac gtt atc gac tac atc ctg gac ctg cag    700
Lys Val Glu Ile Leu Gln His Val Ile Asp Tyr Ile Leu Asp Leu Gln
 90                  95                 100                 105 ctg gcg ctg gag acg cac ccg gcc ctg ctg agg cag cca cca ccg ccc    748
Leu Ala Leu Glu Thr His Pro Ala Leu Leu Arg Gln Pro Pro Pro Pro
                110                 115                 120 gcg ccg cca cac cac ccg gcc ggg acc tgt cca gcc gcg ccg ccg cgg    796
Ala Pro Pro His His Pro Ala Gly Thr Cys Pro Ala Ala Pro Pro Arg
            125                 130                 135
```

```
acc ccg ctc act gcg ctc aac acc gac ccg gcc ggc gcg gtg aac aag       844
Thr Pro Leu Thr Ala Leu Asn Thr Asp Pro Ala Gly Ala Val Asn Lys
        140                 145                 150 cag ggc gac agc att ctg tgc cgc tga gccgcgctgt ccaggtgtgc              891
Gln Gly Asp Ser Ile Leu Cys Arg
        155             160 ggccgcctga gcccgagcca ggagcactag agagggaggg ggaagagcag aagttagaga      951
aaaaaagcca ccggaggaaa ggaaaaaaca tcggccaacc tagaaacgtt ttcattcgtc     1011
attccaagag agagagagga aagaaaaata caactttcat tctttctttg cacgttcata     1071
aacattctac atacgtattc tcttttgtct cttcatttat aactgctgtg aattgtacat     1131
ttctgtgttt tttggaggtg cagttaaact tttaagctta agtgtgacag gactgataaa     1191
tagaagatca agagtagatc cgactttaga agcctacttt gtgaccaagg agctcaattt     1251
ttgttttgaa gctttactaa tctaccagag cattgtagat attttttttt tacatctatt     1311
gtttaaaata gatgattata acggggcaga gaactttctt ttctctgcaa gaatgttaca     1371
tattgtatag ataaatgagt gacatttcat accatgtata tatagagatg ttctataagt     1431
gtgagaaagt atatgcttta atagatactg taattataag atattttaa ttaaatattt      1491
ttttgtaaat attatgtgtg tgtttttttt taatctatgg gaatatttct tttggaaaat     1551
catttttcag ctcaattaca gagctcttga tatcttgaat gtcttttctg tttggcctgg     1611
ctcttaattt gcttttgttt tgcccagtat agactcggaa gtaacagtta tagctagtgg     1671
tcttgcatga ttgcatgaga tgtttaatca caaattaaac ttgttctgag tccattcaaa     1731
tgtgtttttt taaatgtaga ttgaaatctt tgtatttgaa gcatacatgt tgaaaataca     1791
ccttatcagt ttttaagtac agggttttat agtgtaatat atacagagta agtgtttgtt     1851
tttgtttttc aactgaggtc aaaatggatt ctgaatgatt ttgcatatgg gatgaggaaa     1911
tgcttggatc cttaaggagt ttacgaaatc tgctgtttta tcaaagtgaa aaaaaattgc     1971
ttattactct tcatttttaca ctaaagctta atgtcactaa gtttcatgtc tgtacagatt    2031
atttaaatca tggaaatgaa aaaaatgttc tctgcttgct accaaaggac aaactcttgg     2091
aaatgaacac tttctgcttt ccttcctcca agaattaat aggcaacagt gggagaaaaa      2151
aaaggcataa tggcaaatcc ttcaagcagg gataaaagtc gatcttcaaa cattaactta     2211
agcagaccaa aaattctgat gaccgcatct agattttttt tttataaaaa tgattttcac     2271
tatagctatg ttacgctaag ctactgtcca atctcttgtg atgtgtaact tttacatgtg     2331
aatattaaag tagatttctc tgtcttgtac tgtgatttct ggtctcattt ctttaaaacc     2391
ttactcttat ttttctttta aggctctttt ttctccttaa ggaaggtaat attttctagg     2451
ttagatagga ctatcagggt ttgtgaacat tatgcattta atgttatggg tactttacac     2511
acaagttaga tggaattttt agagtgaaag aattaagtag gatttaattg ggtgctttgt     2571
aaatagtcaa ctgtgtgtat aacgtggtct gtttgatttt taaaggaaa ggatttgttt      2631
cagattatac aagaataaaa gtattataga cccaagggac ttcttatgag gtcaaattca     2691
gatatttata tgaatatgaa ataccatggt ccctagtagt cagttgaagt ggcaatgtct     2751
aaacagaaat gaacaaaact aatgctagca ggttaaaatc aatcaaaatg tttaaaaatt     2811
gattctgtcc tcagcatgtt atttcctcag ctctgataat ttactggtct tgagtatttt     2871
gagaatttga tgttgaacgt tataaagtca agaactgct tgtttagatg aggtttattt      2931
ttattttga tattattcat tcttgtcaca catcaagaag aaaacactag agtgctgctg      2991
```

```
gaattccaaa tctgaagaat tctaacgact gcattctttg ttattaaaaa gggcacaatc    3051
cttccttttt atttggcagt ttaatttcag taggaagcat gtcacatgtg cactgttggt    3111
tagaattatg catctgtcat gcctgactgc tgaaccctac ctaagccttt tggcgcagtt    3171
taaaacttat actggtggac tgtgaacctc aaaacaaatg ggtattttg ggttttgagg    3231 atagatgtta ctccttaaag tttgtatttg gggcatgaaa aactactgaa agaagaaaag    3291
tgctacagat actacatttc aaagagttgg catttcct ttggccactc aagcagcatt    3351
tgatgtatct aaagaaacaa agtcattgtt tattttttaa aaaattatat gcagttgtac    3411
aagatactac attccattga aatgttggct atgtcctaac caggcaacca gataacaaaa    3471 acatttgag tcttttatct aggtagttct aattattcag ctacttagtt taacaaagga    3531
aaatatcctg acttctctca tttcatttgt agacttttca ttgtataggc acaaccaaag    3591
agtcagactg gtttaaaact ccagaaggaa aaaagtatc ccacacagtg gatgttgttt    3651
ctaagaatgc tacaaaatcc tgacatctca gacatctcaa tgttaaagga agaaaaaaaa    3711 tacctttca tttcaaagaa ctaatatact ttgatattgt gtaaaccta ctcaagttta    3771 ttgtcaagct ttaactgcct ttttagaact ttttaaaatt tcgagcccac aaatctattg    3831
tattagttgc cttctataac aataaatctt cactgagcaa aaggcaaaaa aaaaaaaaaa    3891
```

<210> SEQ ID NO 16
<211> LENGTH: 161
<212> TYPE: PRT
<213> ORGANISM: Homo sapiens

<400> SEQUENCE: 16

```
Met Lys Ala Val Ser Pro Val Arg Pro Ser Gly Arg Lys Ala Pro Ser
1               5                   10                  15

Gly Cys Gly Gly Gly Glu Leu Ala Leu Arg Cys Leu Ala Glu His Gly
            20                  25                  30

His Ser Leu Gly Gly Ser Ala Ala Ala Ala Ala Ala Ala Ala Ala Ala
        35                  40                  45

Arg Cys Lys Ala Ala Glu Ala Ala Asp Glu Pro Ala Leu Cys Leu
    50                  55                  60

Gln Cys Asp Met Asn Asp Cys Tyr Ser Arg Leu Arg Arg Leu Val Pro
65                  70                  75                  80

Thr Ile Pro Pro Asn Lys Lys Val Ser Lys Val Glu Ile Leu Gln His
                85                  90                  95

Val Ile Asp Tyr Ile Leu Asp Leu Gln Leu Ala Leu Glu Thr His Pro
            100                 105                 110

Ala Leu Leu Arg Gln Pro Pro Pro Ala Pro Pro His His Pro Ala
        115                 120                 125

Gly Thr Cys Pro Ala Ala Pro Pro Arg Thr Pro Leu Thr Ala Leu Asn
    130                 135                 140

Thr Asp Pro Ala Gly Ala Val Asn Lys Gln Gly Asp Ser Ile Leu Cys
145                 150                 155                 160

Arg
```